(12) United States Patent
Sugiura et al.

(10) Patent No.: US 10,961,494 B2
(45) Date of Patent: *Mar. 30, 2021

(54) CELL CULTURE DEVICE AND CELL CULTURE METHOD

(71) Applicant: NATIONAL INSTITUTE OF ADVANCED INDUSTRIAL SCIENCE AND TECHNOLOGY, Tokyo (JP)

(72) Inventors: Shinji Sugiura, Tsukuba (JP); Taku Satoh, Tsukuba (JP); Toshiyuki Kanamori, Tsukuba (JP); Kazumi Shin, Tsukuba (JP)

(73) Assignee: NATIONAL INSTITUTE OF ADVANCED INDUSTRIAL SCIENCE AND TECHNOLOGY

( * ) Notice: Subject to any disclaimer, the term of this patent is extended or adjusted under 35 U.S.C. 154(b) by 275 days.

This patent is subject to a terminal disclaimer.

(21) Appl. No.: 16/082,339

(22) PCT Filed: Mar. 7, 2017

(86) PCT No.: PCT/JP2017/008995
§ 371 (c)(1),
(2) Date: Sep. 5, 2018

(87) PCT Pub. No.: WO2017/154899
PCT Pub. Date: Sep. 14, 2017

(65) Prior Publication Data
US 2019/0093058 A1 Mar. 28, 2019

(30) Foreign Application Priority Data
Mar. 8, 2016 (JP) .............................. JP2016-045023

(51) Int. Cl.
  *C12M 1/00* (2006.01)
  *C12M 1/12* (2006.01)
  *C12M 1/02* (2006.01)

(52) U.S. Cl.
  CPC ............ C12M 23/34 (2013.01); C12M 23/38 (2013.01); C12M 25/02 (2013.01); C12M 27/00 (2013.01); C12M 29/20 (2013.01)

(58) Field of Classification Search
  CPC ...... C12M 23/34; C12M 23/38; C12M 25/02; C12M 27/00
  See application file for complete search history.

(56) References Cited

U.S. PATENT DOCUMENTS

2019/0093058 A1   3/2019  Sugiura
2019/0093059 A1*  3/2019  Sugiura .................. C12M 23/34

FOREIGN PATENT DOCUMENTS

EP     3279310 A1    2/2018
EP     3 428 266 A1  1/2019
(Continued)

OTHER PUBLICATIONS

International Search Report dated Apr. 11, 2017 in corresponding PCT International Application No. PCT/JP2017/008995.
Written Opinion dated Apr. 11, 2017 in corresponding PCT International Application No. PCT/JP2017/008995.
J.W. Scannell et al., Nat. Rev. Drug Discov., 11, 191-200 (2012).
F. Pammolli et al., Nat. Rev. Drug Discov., 10, 428-438 (2011).
(Continued)

*Primary Examiner* — Michael L Hobbs
(74) *Attorney, Agent, or Firm* — Ostrolenk Faber LLP

(57) ABSTRACT

A cell culture device includes a storage tank having one or a plurality of cell culture units. Each of the cell culture units includes a first liquid storage chamber having an airtight structure in which a liquid is to be stored, a second liquid storage chamber in which the liquid is to be stored, a culture liquid storage chamber having a culture liquid storage space in which a culture liquid of cells is to be stored, a permeable membrane having one surface to which the cells are able to
(Continued)

adhere, said one face facing the culture liquid storage space, and a liquid lead-out flow path that introducing the liquid from a space on the other surface side of the membrane into the second liquid storage chamber, the first liquid storage chamber being set as a supply source of the liquid.

17 Claims, 14 Drawing Sheets

(56) References Cited

FOREIGN PATENT DOCUMENTS

| EP | 3428265 A1 | 1/2019 |
|---|---|---|
| JP | 2008-086264 A | 4/2008 |
| JP | 2009-109249 A | 5/2009 |
| JP | 2009-527225 A | 7/2009 |
| JP | 2011-257238 A | 12/2011 |
| JP | 2015-073468 A | 4/2015 |
| WO | WO 2007/098027 A2 | 8/2007 |
| WO | WO 2013/086329 A1 | 6/2013 |

OTHER PUBLICATIONS

P.M. van Midwoud et al., Integr. Biol., 3, 509-521 (2011).
A.M. Ghaemmaghami et al., Drug Discov. Today, 17, 173-181 (2012).
S.N. Bhatia et al., Nat. Biotechnol., 32, 760-772 (2014).
M. Baker, Nature, 471, 661-665 (2011).
J.H. Sung et al., Lab Chip, 13, 1201-1212 (2013).
H.J. Kim et al.,, Lab Chip, 12, 2165-2174 (2012).
M.B. Esch et al., Biomed. Microdevices, 14, 895-906 (2012).
K.-J. Jang et al., Integr. Biol., 5, 1119-1129 (2013).
R. Booth et al., Lab Chip, 12, 1784-1792 (2012).
S. Sugiura, et al., Anal. Chem., 82, 8278-8282 (2010).
S. Sugiura, et al., Biotechnol. Bioeng., 100, 1156-1165 (2008).
K. Hattori et al., J. Biosci. Bioeng., 118, 327-332 (2014).
Y. Imura et al., Anal. Chem., 82, 9983-9988 (2010).
A.R. Perestrelo et al., Sensors, 15, 31142-31170 (2015).
U.S. Non-Final Office Action, dated Aug. 17, 2020, issued in corresponding U.S. Appl. No. 16/082,345 Total 11 pages.
International Search Report dated Apr. 11, 2017 in corresponding PCT International Application No. PCT/JP2017/008947.
Written Opinion dated Apr. 11, 2017 in corresponding PCT International Application No. PCT/JP2017/008947.

* cited by examiner

CELL CULTURE DEVICE AND CELL CULTURE METHOD

CROSS-REFERENCE TO RELATED APPLICATIONS

The present application is a 35 U.S.C. §§ 371 national phase conversion of PCT/JP2017/008995, filed Mar. 7, 2017, which claims priority to Japanese Patent Application No. 2016-045023, filed Mar. 8, 2016, the contents of which are incorporated herein by reference. The PCT International Application was published in the Japanese language.

TECHNICAL FIELD

The present invention relates to a device that cultures cells and a method of culturing cells using the device.

BACKGROUND ART

As described in Non-Patent Documents 1 and 2, development cost for pharmaceutical products in recent years has increased exponentially, and the success rate of clinical trials has decreased year by year. In addition, the cost for developing chemical products such as cosmetics has similarly increased. As the reason for this, for example, due to the species difference between animals and humans, results of animal experiments cannot be directly extrapolated to clinical trials. In addition, in the development of chemical products such as cosmetics, in some cases, it is difficult to use experimental animals, especially in Europe. Under such circumstances, there are increasing expectations for in vitro cell assays of pharmaceutical candidate compounds and chemical products in which human-derived cultured cells are used.

On the other hand, monolayer culture used in cell assays in the conventional art is often problematic in that the environment surrounding cells is greatly different from the in vivo environment, and therefore, many functions expressed in a body are lost in cultured cells. Advances in a micro-processing technique and three-dimensional culture techniques in recent years have overcome this problem, and it is expected that throughput and reliability of cell assays will be simultaneously improved (for example, Non-Patent Documents 3 and 4). In particular, the concept of organ-on-a-chip, which handles a microfluidic device that reproduces a physiological three-dimensional culture environment in vitro as an organ, has expanded, and research considering application to development of pharmaceutical products is being globally developed (for example, Non-Patent Documents 5 and 6). Furthermore, the concept of body-on-a-chip, which aims to reproduce an individual response by connecting a plurality of organ models reconstituted in vitro with each other through micro flow paths or the like, has also been proposed and has been rapidly attracting attention (for example, Non-Patent Document 7).

As described above, it is expected that the reliability of cellular assays will be improved by reconstituting an organ model formed of human-derived cultured cells in vitro and reproducing physiological functions.

Most organs constituting a living body have a membrane type structure. For example, nutrients are absorbed across the mesentery in the small intestine, and metabolites and waste products are excreted in the kidneys via renal tubular epithelial cell membranes. In addition, oxygen or nutrients are supplied to surrounding tissues through the vessel wall even in blood vessels circulating in the whole body, and waste products are excreted. Membrane type culture containers such as BOYDEN CHAMBER and TRANSWELL have been used to reconstitute functions of such membrane type organs in vitro. However, in these culture containers, a liquid cannot flow on one surface side and the other surface side of the membrane. Therefore, there are problems in that a physiological function is not exhibited, the conditions of cells in the lower portion of the membrane are deteriorated, and the culture containers cannot be applied to body-on-a-chip in which a plurality of organs are linked to each other.

In order to solve these problems, organ-on-a-chip in which a membrane is disposed in a micro flow path has been reported. For example, in vitro models for the intestines (Non-Patent Documents 8 and 9), the kidneys (Non-Patent Document 10), and encephalic blood vessels (Non-Patent Document 11) have been reported. In order to use organ-on-a-chip including such a membrane for drug discovery as an alternative to animal experiments, a system that can simultaneously evaluate many kinds of compounds is necessary. On the other hand, a syringe pump or a peristaltic pump is used for liquid transfer in the above-described prior research, and therefore, it is difficult to parallelize the culture system.

The present inventors or the like have already developed a "pressure-driven type perfusion culture micro-chamber array" capable of conveniently handling a large number of drug solutions in studies so far (Non-Patent Documents 12 and 13). Then, they have developed a circulation culture system with a convenient platform and performed a user evaluation for practical use (Non-Patent Document 14 and Patent Document 1).

PRIOR ART DOCUMENTS

Patent Documents

[Patent Document 1] Japanese Unexamined Patent Application, First Publication No. 2015-073468

Non-Patent Documents

[Non-Patent Document 1] Scannell, J. W. et al. Nat. Rev. Drug Discov., 11, 191 (2012)
[Non-Patent Document 2] Pammolli, F. et al. Nat. Rev. Drug Discov., 10, 428 (2011)
[Non-Patent Document 3] van Midwoud, P. M. et al. Integr. Biol., 3, 509 (2012)
[Non-Patent Document 4] Ghaemmaghami, A. M. et al. Drug Discov. Today, 17, 173 (2012)
[Non-Patent Document 5] Bhatia, S. N. et al. Nat. Biotechnol., 32, 760 (2014)
[Non-Patent Document 6] Baker, M. Nature, 471, 661 (2011)
[Non-Patent Document 7] Sung, J. H. et al. Lab Chip, 13, 1201 (2013)
[Non-Patent Document 8] H. J. Kim, D. Huh, G. Hamilton and D. E. Ingber, Lab Chip, 12, 2165-2174 (2012).
[Non-Patent Document 9] M. B. Esch, J. H. Sung, J. Yang, C. H. Yu, J. J. Yu, J. C. March and M. L. Shuler, Biomed. Microdevices, 14, 895-906 (2012).
[Non-Patent Document 10] K.-J. Jang, A. P. Mehr, G. A. Hamilton, L. A. McPartlin, S. Chung, K.-Y. Suh and D. E. Ingber, Integr. Biol., 5, 1119-1129 (2013).
[Non-Patent Document 11] R. Booth and H. Kim, Lab Chip, 12, 1784-1792 (2012).
[Non-Patent Document 12] S. Sugiura, et al., Anal. Chem., 82, 8278 (2010)

[Non-Patent Document 13] S. Sugiura, et al., Biotechnol. Bioeng., 100, 1156 (2008)

[Non-Patent Document 14] K. Hattori, et al., J. Biosci. Bioeng., 118, 327 (2014)

SUMMARY OF THE INVENTION

Problems to be Solved by the Invention

In a cell culture device in the conventional art, since the structure of piping or the like is complicated, there are many problems such as an increase in size of the device or a complicated operation.

An object of the present invention is to provide a cell culture device which has a simple structure and is easy to operate, and a cell culture method.

Means for Solving the Problems (1) A cell culture device including: a storage tank having one or a plurality of cell culture units, in which each of the cell culture units includes a first liquid storage chamber having an airtight structure in which a liquid is to be stored, a second liquid storage chamber in which the liquid is to be stored, a culture liquid storage chamber having a culture liquid storage space in which a culture liquid of cells is to be stored, a permeable membrane having one surface to which the cells are able to adhere, said one face facing the culture liquid storage space, and a liquid lead-out flow path that introduces the liquid from a space on the other surface side of the membrane into the second liquid storage chamber, the first liquid storage chamber being a supply source of the liquid, and the storage tank has a vent hole through which gas is supplied to and discharged from the first liquid storage chamber.

(2) The cell culture device according to (1), in which at least two of the first liquid storage chambers in the plurality of the cell culture units are connected with each other so that gas is able to flow therethrough.

(3) The cell culture device according to (1), further including: a liquid return flow path which introduces the liquid from the second liquid storage chamber into the first liquid storage chamber, in which the second liquid storage chamber has a cell-holding portion in which seeded cells are to be held.

(4) The cell culture device according to (3), in which at least two of the first liquid storage chambers in the plurality of the cell culture units are connected with each other so that gas is able to flow therethrough and at least two of the second liquid storage chambers in the plurality of the cell culture units are connected with each other so that gas is able to flow therethrough.

(5) The cell culture device according to any one of (1) to (4), in which each of the cell culture units further includes a second culture liquid storage chamber in which the culture liquid is stored, a culture liquid lead-out flow path that introduces the culture liquid from the culture liquid storage chamber into the second culture liquid storage chamber, and a culture liquid introduction flow path that introduces the culture liquid from the second culture liquid storage chamber into the culture liquid storage chamber, and the storage tank has a vent hole through which gas is supplied to and discharged from the culture liquid storage chamber.

(6) The cell culture device according to (5), in which at least two of the culture liquid storage chambers in the plurality of the cell culture units are connected with each other so that gas is able to flow therethrough.

(7) The cell culture device according to (5) or (6), in which the first liquid storage chamber, the second liquid storage chamber, and the second culture liquid storage chamber each have a cell-holding portion in which seeded cells are to be held.

(8) The cell culture device according to any one of (1) to (7), further including: a backflow prevention mechanism that controls flow of the liquid from the liquid lead-out flow path to the second liquid storage chamber.

(9) The cell culture device according to (8), in which the backflow prevention mechanism is a check valve which allows the flow of the liquid in a direction from the liquid lead-out flow path to the second liquid storage chamber and prevents flow in an opposite direction thereof.

(10) The cell culture device according to any one of (1) to (7), further including: a liquid introduction flow path that introduces the liquid from the first liquid storage chamber into a space on the other surface side of the membrane; and a backflow prevention mechanism that controls flow of the liquid from the first liquid storage chamber to the liquid introduction flow path.

(11) The cell culture device according to (10), in which the backflow prevention mechanism is a Laplace valve which allows the flow of the liquid from the first liquid storage chamber to the liquid introduction flow path and prevents flow of gas from the first liquid storage chamber to the liquid introduction flow path.

(12) The cell culture device according to any one of (1) to (11), in which the liquid lead-out flow path has a resistance flow path part of which a flow path cross-sectional area is less than or equal to $1/10$ of that of the other part.

(13) The cell culture device according to any one of (1) to (12), in which the storage tank has a container-shaped tank main body in which the first liquid storage chamber, the second liquid storage chamber, and the culture liquid storage chamber are formed, and a lid portion that airtightly closes openings of the first liquid storage chamber, the second liquid storage chamber, and the culture liquid storage chamber in an openable manner.

(14) The cell culture device according to (13), further including: a lid portion-pressing portion that holds the lid portion by pressing the lid portion toward the tank main body, in which the lid portion-pressing portion has a pressing member that presses the lid portion toward the tank main body.

(15) The cell culture device according to (13) or (14), in which the tank main body includes a bottom plate having the liquid lead-out flow path, and a wall portion provided on one surface of the bottom plate, and the first liquid storage chamber, the second liquid storage chamber, and the culture liquid storage chamber are spaces partitioned by the bottom plate and the wall portion.

(16) The cell culture device according to (15), further including: a wall portion-pressing portion that holds the wall portion by pressing the wall portion toward the bottom plate, in which the wall portion-pressing portion has a pressing member that presses the wall portion toward the bottom plate.

(17) The cell culture device according to any one of (1) to (16), further including: pressurizing means capable of pressurizing an inside of the first liquid storage chamber.

(18) A cell culture method, using a cell culture device including a storage tank having one or a plurality of cell culture units, in which each of the cell culture units includes a first liquid storage chamber having an airtight structure in which a liquid is to be stored, a second liquid storage chamber in which the liquid is to be stored, a culture liquid storage chamber having a culture liquid storage space in which a culture liquid of cells is to be stored, a permeable membrane having one surface to which the cells are able to adhere where said one face faces the culture liquid storage space, and a liquid lead-out flow path that introduces the liquid from a space on the other surface side of the membrane into the second liquid storage chamber, the first liquid storage chamber being set as a supply source of the liquid, the storage tank having a vent hole through which gas is supplied to and discharged from the first liquid storage chamber, the method including: supplying gas to the first liquid storage chamber through the vent hole to pressurize an inside of the first liquid storage chamber; and introducing the liquid from a space on the other surface side of the membrane into the second liquid storage chamber through the liquid lead-out flow path with a pressure increase in the first liquid storage chamber.

Effects of Invention

According to an aspect of the present invention, it is possible to introduce the liquid from the space on the other surface side of the membrane into the second liquid storage chamber, and therefore, to simplify the structure of the flow path for liquid transfer. For this reason, it is possible to miniaturize the device by simplifying the structure of the device and to facilitate the operation.

According to the cell culture device having a plurality of cell culture units, it is possible to perform a plurality of tests in parallel through a simple operation. For this reason, it is possible to efficiently evaluate a large number of specimens (drugs and the like).

EMBODIMENTS FOR CARRYING OUT THE INVENTION

First Embodiment

[Cell Culture Device]

A cell culture device 10 according to a first embodiment will be described with reference to the drawings.

Figure 1:
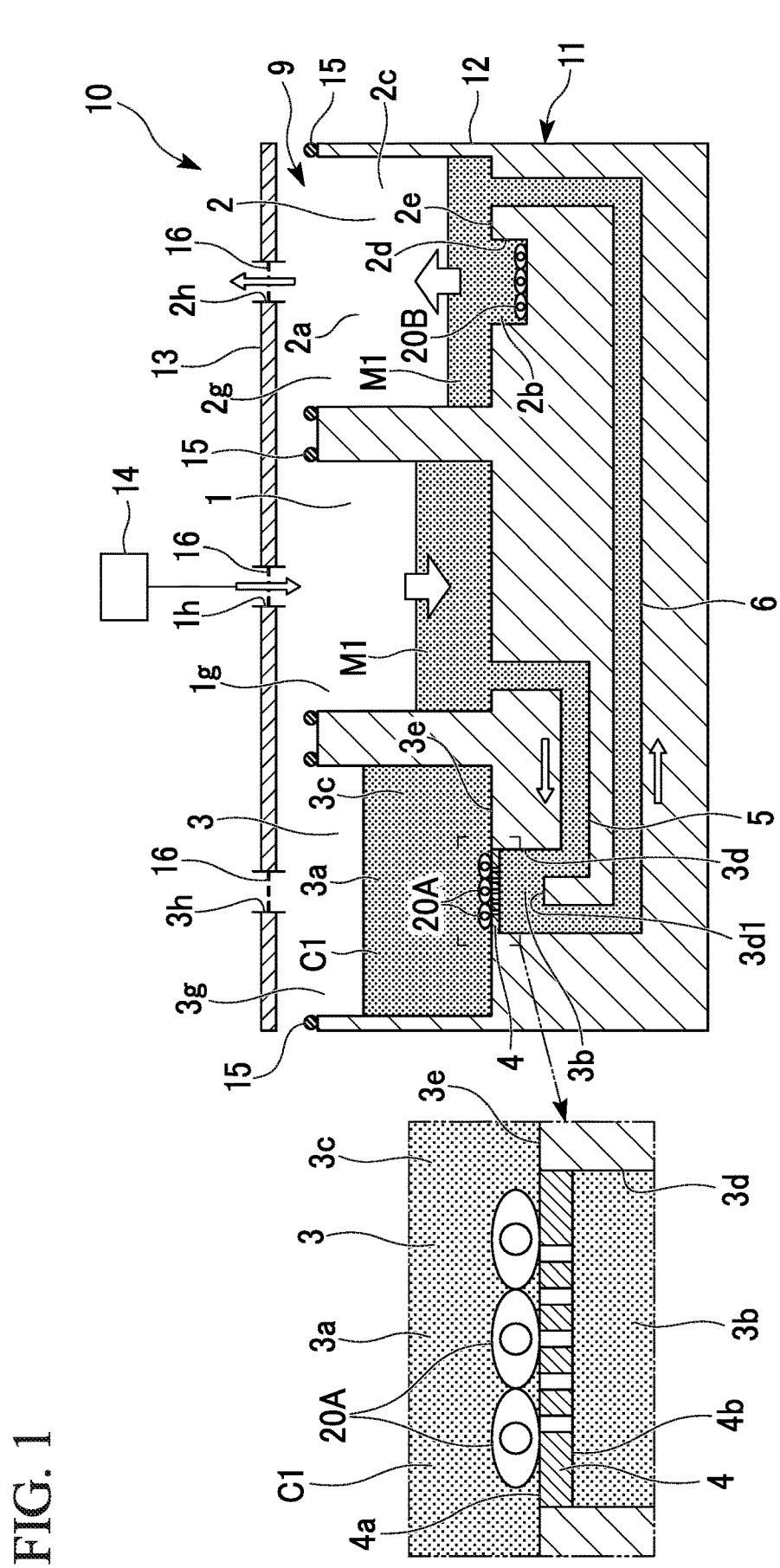
FIG. 1 is a cross-sectional view schematically showing a cell culture device according to a first embodiment.
Figure 2A:
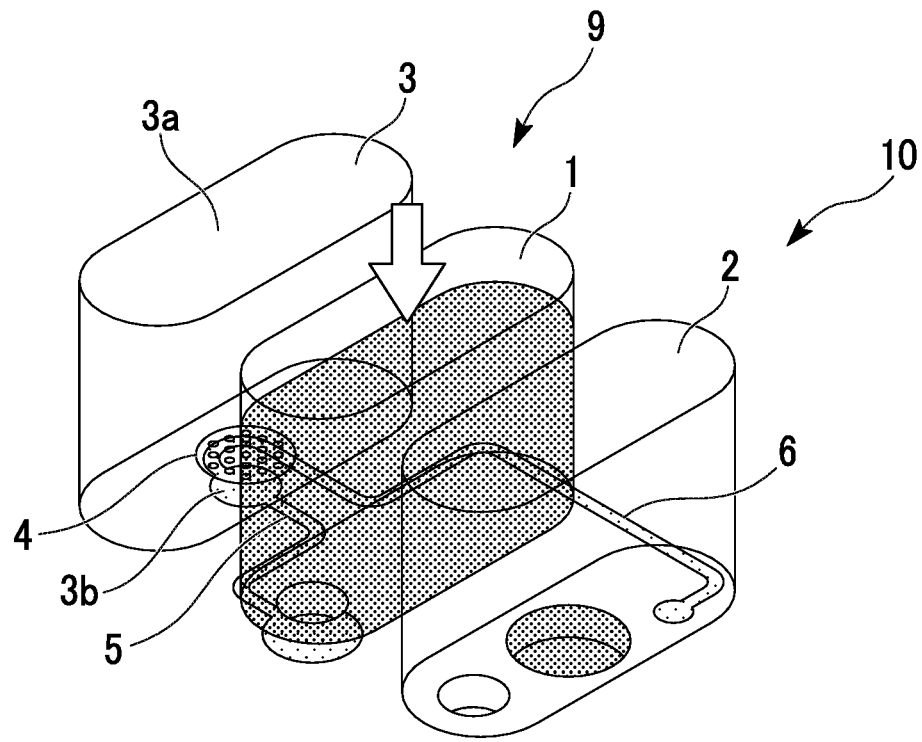
FIG. 2A is a perspective view schematically showing the cell culture device of FIG. 1.
Figure 2B:
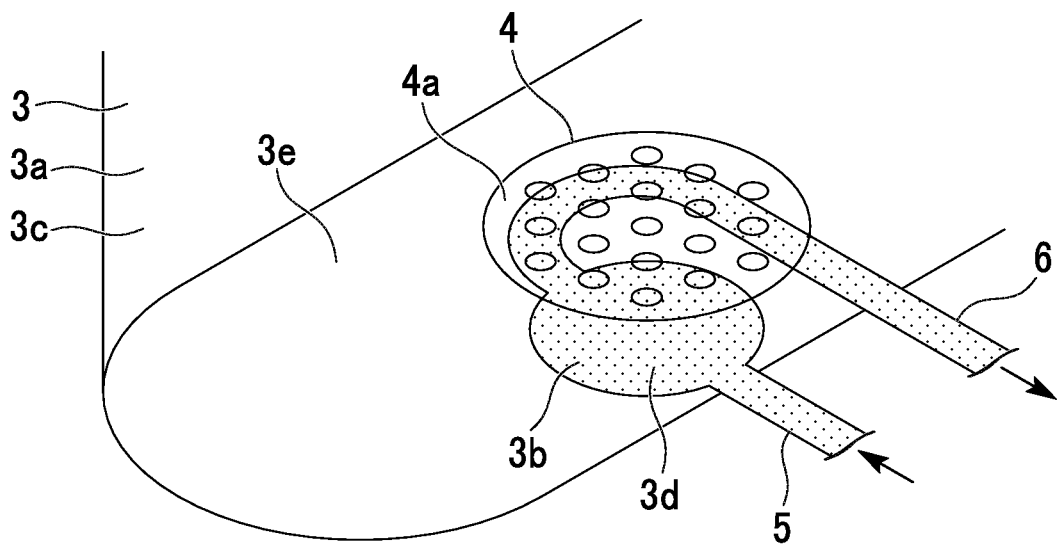
FIG. 2B is an enlarged view showing a part of the cell culture device of FIG. 1.

FIG. 1 is a cross-sectional view schematically showing the cell culture device 10. FIG. 2A is a perspective view schematically showing the cell culture device 10. FIG. 2B is an enlarged view showing a part of the cell culture device 10.

As shown in FIGS. 1, 2A, and 2B, the cell culture device 10 includes a storage tank 11 and a pressurizing pump 14. The storage tank 11 includes one cell culture unit 9. The storage tank 11 includes a container-shaped tank main body 12 and a lid portion 13.

The cell culture unit 9 has a first liquid storage chamber 1, a second liquid storage chamber 2, a culture liquid storage chamber 3, a membrane 4, a liquid introduction flow path 5, and a liquid lead-out flow path 6. The first liquid storage chamber 1 and the second liquid storage chamber 2 are spaces formed by recess portions formed on the upper surface of the tank main body 12 of the storage tank 11 and are capable of storing a liquid medium M1 (liquid).

The second liquid storage chamber 2 has a main chamber 2c and a cell-holding recess portion 2d (cell-holding portion) formed on a bottom surface 2e of the main chamber 2c. Cells 20B are held in the cell-holding recess portion 2d. The internal space of the second liquid storage chamber 2 is a culture liquid storage space 2a.

The culture liquid storage chamber 3 is a space formed by a recess portion formed on the upper surface of the tank main body 12 of the storage tank 11 and has a main chamber 3c and a recess portion 3d formed on the bottom surface 3e of the main chamber 3c. The internal space of the main chamber 3c is a culture liquid storage space 3a. The space partitioned by the inner surface of the recess portion 3d and an outer surface 4b of the membrane 4 is an outer surface side space 3b. In FIG. 1, the outer surface side space 3b is positioned below the culture liquid storage space 3a. The culture liquid storage chamber 3 is capable of storing a culture liquid C1 in the culture liquid storage space 3a.

Substances having a predetermined size or less are permeable through the membrane 4 in a thickness direction. The movement of substances permeating through the membrane 4 occurs, for example, by diffusion. In some cases, the substance movement may be promoted by an action of the cells 20 attached to the membrane 4. The membrane 4 may be, for example, a porous membrane. The average pore diameter of the membrane 4 is, for example, 0.1 μm to 10 μm. The material of the membrane 4 may be any one of polycarbonate, polyester, and silicone resin. The membrane 4 may be, for example, a semipermeable membrane. The cells 20 are not permeable through the membrane 4. An inner surface 4a of the membrane 4 is preferably coated with a cell adhesive material. The cell adhesive material is preferably one or two or more of collagen, gelatin, fibronectin, laminin, vitronectin, matrigel, and polylysine.

The membrane 4 is installed in the culture liquid storage chamber 3 so as to separate the culture liquid storage space 3a and the outer surface side space 3b from each other. The membrane 4 is located at a position higher than that of the bottom surface of the recess portion 3d and can be installed so as to close the upper opening of the recess portion 3d along the bottom surface 3e of the main chamber 3c. The inner surface 4a (one surface) of the membrane 4 faces the culture liquid storage space 3a, and the outer surface 4b (the other surface) faces the outer surface side space 3b.

One end of the liquid introduction flow path 5 is connected to the bottom portion of the first liquid storage chamber 1, and the other end is connected to a bottom portion 3d1 of the recess portion 3d of the culture liquid storage chamber 3. The liquid introduction flow path 5 is capable of introducing the liquid medium M1 from the first liquid storage chamber 1 into the outer surface side space 3b of the culture liquid storage chamber 3.

One end of the liquid lead-out flow path 6 is connected to the bottom portion 3d1 of the recess portion 3d of the culture liquid storage chamber 3, and the other end is connected to the bottom portion of the main chamber 2c of the second liquid storage chamber 2. The liquid lead-out flow path 6 is capable of introducing the liquid medium M1 from the outer surface side space 3b of the culture liquid storage chamber 3 into the second liquid storage chamber 2.

The lid portion 13 airtightly closes the opening of the tank main body 12 in an openable manner. Specifically, the lid portion 13 is capable of airtightly closing upper openings 1g, 2g, and 3g of the first liquid storage chamber 1, the second liquid storage chamber 2, and the culture liquid storage chamber 3. An example of a structure in which the lid portion 13 airtightly closes the upper openings 1g, 2g, and 3g includes a structure in which the lid portion 13 abuts on the upper surface of the tank main body 12 with a packing 15 interposed therebetween, and the packing 15 provided so as to surround each of the upper openings 1g, 2g, and 3g. In FIG. 1, the lid portion 13 is shown separately from the tank main body 12.

The lid portion 13 has vent holes 1h, 2h, and 3h at positions corresponding to the first liquid storage chamber 1, the second liquid storage chamber 2, and the culture liquid storage chamber 3, respectively. It is possible to supply gas (for example, air) to the storage chambers 1, 2, and 3 and to discharge gas (for example, air) from the storage chambers 1, 2, and 3 through the vent holes 1h, 2h, and 3h, respectively. It is preferable that an air filter 16 be provided in each of the vent holes 1h, 2h, and 3h. It is possible to prevent foreign substances from being mixed in the first liquid storage chamber 1, the second liquid storage chamber 2, and the culture liquid storage chamber 3, using the air filter 16.

The pressurizing pump 14 is, for example, a compressor.

[Cell Culture Method]

Next, an example of a method of culturing cells using the cell culture device 10 will be described.

Cells to be cultured in this embodiment are not particularly limited, and it is possible to use, for example, cells derived from animals including humans, cells derived from plants, and cells derived from microorganisms depending on the purpose.

(1) Step 1

As shown in FIGS. 1, 2A, and 2B, cells 20A are seeded on the inner surface 4a of the membrane 4 and are made to adhere thereto, and a liquid medium (culture liquid C1) is introduced into the culture liquid storage space 3a of the culture liquid storage chamber 3. In addition, the liquid medium M1 is introduced into the first liquid storage chamber 1. The liquid medium M1 can also be introduced into the second liquid storage chamber 2. In addition, the cells 20B different from the cells 20A can be seeded in the second liquid storage chamber 2. Then, the lid portion 13 is closed so as to be pressed against the packing 15, and at least the upper opening 1g of the first liquid storage chamber 1 is airtightly closed.

(2) Step 2

The pressurizing pump 14 is operated to pressurize the inside of the first liquid storage chamber 1 by supplying gas (for example, air) to the first liquid storage chamber 1 through the vent hole 1h. At this time, it is preferable that the second liquid storage chamber 2 be open to the atmosphere through the vent hole 2h. Due to the pressure increase in the first liquid storage chamber 1, the liquid medium M1 in the first liquid storage chamber 1 (supply source) is introduced into the outer surface side space 3b through the liquid introduction flow path 5. The liquid medium M1 in the outer surface side space 3b is introduced into the second liquid storage chamber 2 through the liquid lead-out flow path 6.

The flow of the liquid medium M1 in the outer surface side space 3b is opposed to the liquid medium (culture liquid C1) introduced into the culture liquid storage space 3a of the culture liquid storage chamber 3 while interposing the membrane 4. That is, the liquid medium (culture liquid C1) can be supplied to the liquid medium M1 in the outer surface side space 3b depending on selection of the membrane 4.

It is considered that the cell culture method according to the present embodiment can be specifically applied to, for example, the following test.

Cells in the intestines are used as the cells 20A to be seeded on the membrane 4 in the culture liquid storage chamber 3. It is possible to improve adhesiveness of the cells 20A by coating the membrane 4 with collagen in advance. By culturing the cells 20A for several days (for example, 3 days) using the membrane 4 coated with collagen, the cells 20A (cells of the intestines) proliferate in a membrane shape on the surface of the membrane 4, and cell layers, such as the culture liquid C1 side being an apical side and the collagen-coated side being a basal side, which have polarity are formed.

In the second liquid storage chamber 2, cancer cells are used as the cells 20B. The cells 20B are seeded and cultured in the cell-holding recess portion 2d.

The influence of a substance as a specimen on the cells 20A and 20B can be evaluated by adding the substance into the system (for example, the culture liquid storage space 3a in the culture liquid storage chamber 3). Examples of the substance as a specimen include chemical substances, such as pharmaceutical candidate compounds, food additives, cosmetic raw materials, paints, and agricultural chemicals, which are used in various chemical products. The specimen is not limited thereto.

Here, an anticancer agent is added to the culture liquid storage space 3a of the culture liquid storage chamber 3 as a specimen.

A part of the specimen that has passed through the layers formed of the cells 20A of the intestines on the membrane 4 permeates through the membrane 4 and is mixed into the liquid medium M1 in the outer surface side space 3b. By pressurizing the first liquid storage chamber 1, the liquid medium M1 containing the substance flows into the second liquid storage chamber 2 through the liquid lead-out flow path 6, and comes into contact with the cells 20B (cancer cells) in the second liquid storage chamber 2.

In this test, it is possible to evaluate the absorption of the anticancer agent through the intestines and an anticancer effect thereof at the same time.

In a test using a culture container, such as a culture dish or a microplate, in the conventional art, it is necessary to evaluate the anticancer effect by collecting an anticancer agent absorbed through the intestines and making the anticancer agent act on cancer cells cultured using another culture container. Therefore, a two-step culture operation is necessary.

It is possible to evaluate a specimen with a single operation using the cell culture device 10. In addition, it is possible to make an anticancer agent absorbed through the intestines (cells 20A) act on the cancer cells (cells 20B) in real time, and therefore, it is particularly useful when evaluating the absorption of chemically unstable substances and the anticancer effect.

By pressurizing the first liquid storage chamber 1, the cell culture device 10 can transfer the liquid medium M1 to the second liquid storage chamber 2 through the liquid introduction flow path 5 via the outer surface side space 3b. In the cell culture device 10, the structure of the flow paths for liquid transfer can be simplified. Therefore, it is possible to miniaturize the device by simplifying the structure of the device and to facilitate an operation such as setting of the device.

For example, in the devices shown in Non-Patent Documents 8, 10, and 11, structures are employed in which a syringe pump and a cartridge-type peristaltic pump are used for liquid transfer. Therefore, the piping connection for liquid transfer is more complicated compared to that of the present embodiment, the device increases in size, and an operation of the test is more complicated as well.

Second Embodiment

[Cell Culture Device]

A cell culture device 10A according to a second embodiment will be described with reference to the drawings. Hereinafter, the same configurations as those described above are given the same reference numerals, and the description thereof will not be repeated.

Figure 3:
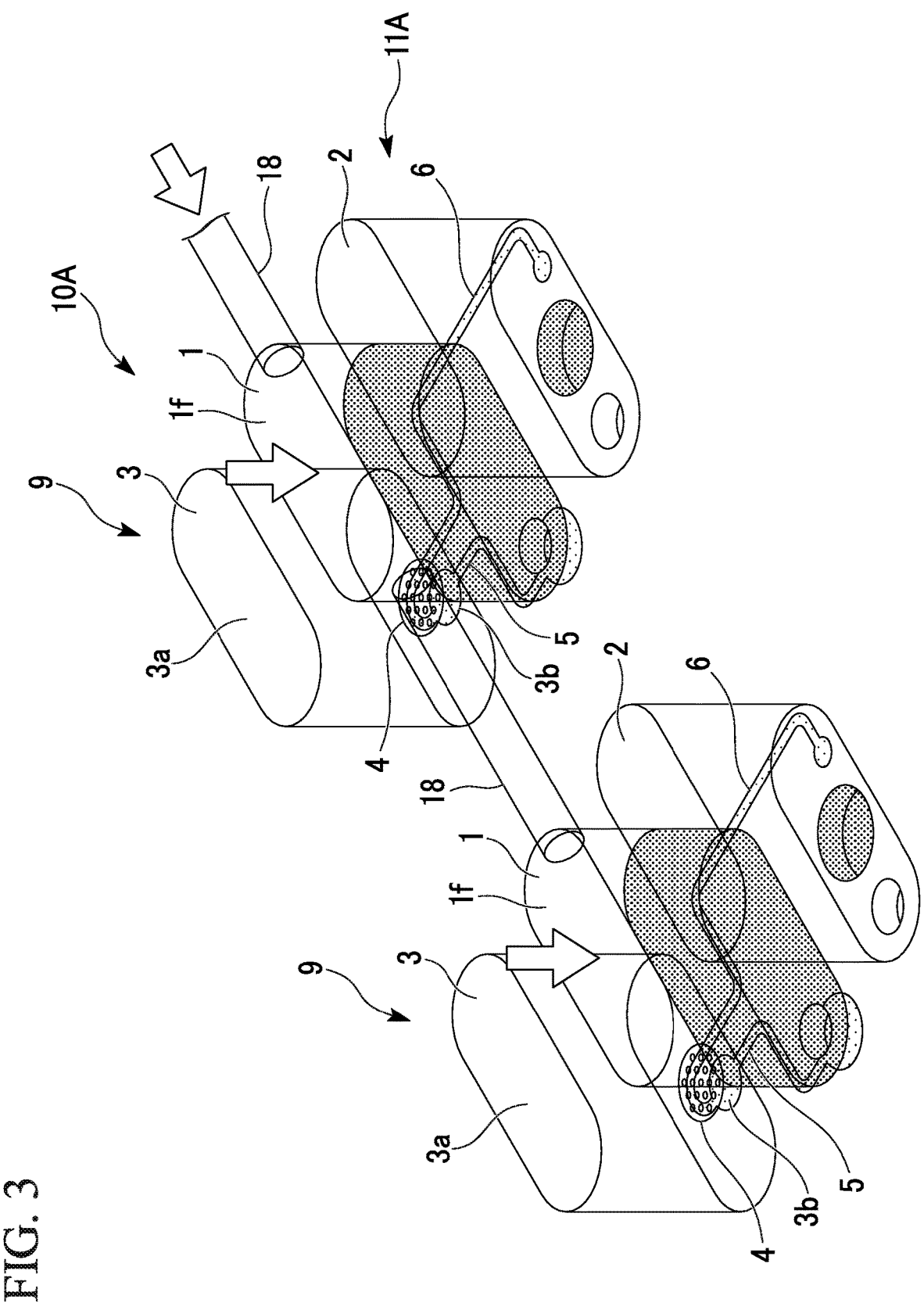
FIG. 3 is a perspective view schematically showing a cell culture device according to a second embodiment.

As shown in FIG. 3, a storage tank 11A in the cell culture device 10A has a plurality of cell culture units 9. The number of cell culture units 9 may be any number of two or more.

Among the plurality of cell culture units 9, first liquid storage chambers 1 and 1 of two adjacent cell culture units 9 and 9 are connected with each other through a gas flow path 18. One end and the other end of the gas flow path 18 are connected to upper gas phase spaces 1f and 1f in the first liquid storage chambers 1 and 1, and therefore, the gas flow path 18 is connected to the first liquid storage chambers 1 and 1 so that gas is able to flow therethrough. In a case where the number of cell culture units 9 is three or more, first liquid storage chambers 1 of at least two cell culture units 9 may be connected with each other through a gas flow path 18.

In the cell culture device 10A, when some first liquid storage chambers 1 out of the plurality of first liquid storage chambers 1 are pressurized, all the first liquid storage chambers 1 connected to each other through the gas flow path 18 are collectively pressurized. Therefore, it is possible to transfer a liquid medium M1 to a second liquid storage chamber 2 via an outer surface side space 3b of a culture liquid storage chamber 3. For this reason, in the cell culture device 10A, it is possible to perform a plurality of tests in parallel through a simple operation.

In addition, a liquid can be transferred by a small number of pressurizing pumps 14 (refer to FIG. 1), and therefore, the structure of the device can be simplified. For this reason, it is possible to miniaturize the device by simplifying the structure of the device and to facilitate the operation such as setting of the device.

In the devices shown in Non-Patent Documents 8, 10, and 11 described above, structures are employed in which a syringe pump and a cartridge-type peristaltic pump are used for liquid transfer, and one pump and one organ-on-a-chip are used in order to evaluate one specimen.

In order to evaluate a plurality of specimens with this structure, it is necessary to add as many pumps and peristaltic pump cartridges as the number of specimens to be examined. Therefore, the number of piping connections for liquid transfer increases.

The cell culture device 10A shown in FIG. 3 is superior to the devices shown in Non-Patent Documents 8, 10, 11, and the like in that it is possible to evaluate a large number of specimens (drugs and the like) at the same time through a simple operation.

Third Embodiment

[Cell Culture Device]

A cell culture device 10E according to a third embodiment will be described with reference to the drawings.

Figure 4:
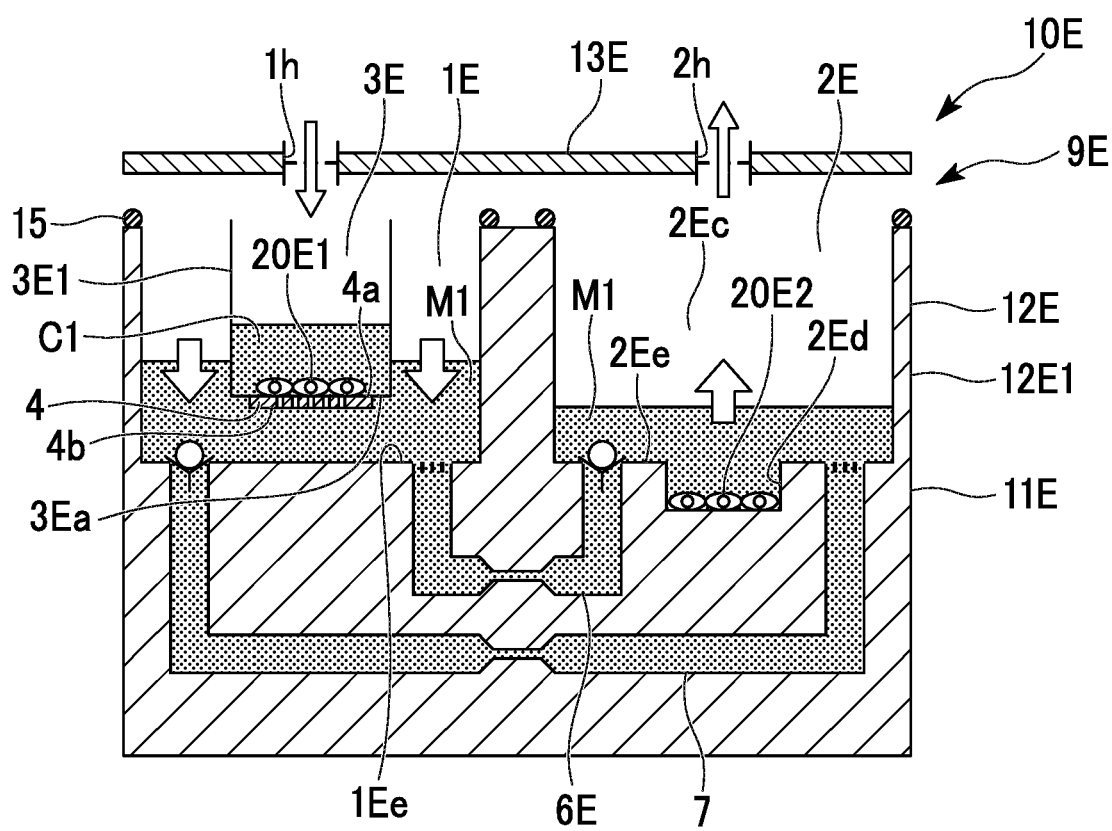
FIG. 4 is a cross-sectional view schematically showing a cell culture device according to a third embodiment.

As shown in FIG. 4, a storage tank 11E of the cell culture device 10E includes a tank main body 12E and a lid portion 13E. The storage tank 11E includes a cell culture unit 9E. The cell culture unit 9E has a first liquid storage chamber 1E, a second liquid storage chamber 2E, a culture liquid storage chamber 3E, a membrane 4, a liquid lead-out flow path 6E, and a liquid return flow path 7.

The tank main body 12E includes a main portion 12E1 in which the first liquid storage chamber 1E and the second liquid storage chamber 2E are formed, and a culture liquid storage tank 3E1. The culture liquid storage chamber 3E is an internal space of the culture liquid storage tank 3E1.

The second liquid storage chamber 2E has a main chamber 2Ec and a cell-holding recess portion 2Ed (cell-holding portion) formed on a bottom surface 2Ee of the main chamber 2Ec.

Cells 20E2 are held in the cell-holding recess portion 2Ed.

The membrane 4 is provided in a bottom portion 3Ea of the culture liquid storage chamber 3E.

The culture liquid storage tank 3E1 is accommodated in the first liquid storage chamber 1E. The culture liquid storage tank 3E1 is positioned upwardly away from a bottom surface 1Ee of the first liquid storage chamber 1E. For this reason, the space between the bottom surface 1Ee of the first liquid storage chamber 1E and the membrane 4 is a space on an outer surface 4b side of the membrane 4.

The lid portion 13E has vent holes 1h and 2h at positions corresponding to the first liquid storage chamber 1E and the second liquid storage chamber 2E, respectively.

The cell culture device 10E can lead out a liquid medium M1 from the first liquid storage chamber 1E to the second liquid storage chamber 2E by pressurizing the first liquid storage chamber 1E. That is, gas (for example, air) is supplied to the first liquid storage chamber 1E through the vent hole 1h of the lid portion 13E to pressurize the inside of the first liquid storage chamber 1E, whereby the liquid medium M1 can be led out from the first liquid storage chamber 1E to the second liquid storage chamber 2E through the liquid lead-out flow path 6E.

Similarly, it is possible to transfer the liquid culture M1 from the second liquid storage chamber 2E to the first liquid storage chamber 1E by pressurizing the second liquid storage chamber 2E. That is, gas (for example, air) is supplied to the second liquid storage chamber 2E through the vent hole 2h of the lid portion 13E to pressurize the inside of the second liquid storage chamber 2E, whereby the liquid medium M1 can be led out from the second liquid storage chamber 2 to the first liquid storage chamber 1E through the liquid return flow path 7.

[Cell Culture Method]

Next, an example of a method of culturing cells using the cell culture device 10E will be described.

(1) Step 1

Cells 20E1 are seeded on an inner surface 4a of the membrane 4 of the culture liquid storage chamber 3. Cells 20E2 are seeded in the cell-holding recess portion 2Ed of the second liquid storage chamber 2E.

(2) Step 2

After the liquid medium M1 is introduced into the first liquid storage chamber 1E and the second liquid storage chamber 2E and a culture liquid C1 is introduced into the culture liquid storage chamber 3E, the lid portion 13E is closed.

(3) Step 3

The inside of the first liquid storage chamber 1E is pressurized by supplying gas (for example, air) to the first liquid storage chamber 1E through the vent hole 1h of the lid portion 13E. The second liquid storage chamber 2E is open to the atmosphere through the vent hole 2h. Due to the pressure increase in the first liquid storage chamber 1E, the liquid medium M1 in the first liquid storage chamber 1E is introduced into the second liquid storage chamber 2E through the liquid lead-out flow path 6E.

(4) Step 4

The inside of the second liquid storage chamber 2E is pressurized by supplying gas (for example, air) to the second liquid storage chamber 2E through the vent hole 2h of the lid portion 13E. The first liquid storage chamber 1E is open to the atmosphere through the vent hole 1h. Due to the pressure increase in the second liquid storage chamber 2E, the liquid medium M1 in the second liquid storage chamber 2E is returned to the first liquid storage chamber 1E through the liquid return flow path 7.

By repeating the steps 3 and 4, it is possible to circulate the liquid medium M1 between the first liquid storage chamber 1E and the second liquid storage chamber 2E.

By adding a substance as a specimen to a system (for example, the culture liquid storage chamber 3E) using the cell culture device 10E with cells of the intestines as the cells 20E1 to be seeded in the membrane 4 in the culture liquid storage chamber 3E and with cancer cells as the cells 20E2 to be cultured in the second liquid storage chamber 2, it is possible to evaluate the absorption of this substance through the intestines and the action on the cancer cells at the same time.

By repeating the steps 3 and 4, it is possible to cause the substance absorbed through the membranes of the cells 20E1 of the intestines to continuously accumulate on the liquid culture M1 and act on the cells 20E2 (cancer cells), and therefore, it is possible to detect the action of the specimen on the cancer cells with a higher sensitivity than that of the cell culture device 10 with the configuration of FIG. 1.

In the cell culture device 10E, the structure of the flow paths for liquid transfer can be simplified. Therefore, it is possible to miniaturize the device by simplifying the structure of the device and to facilitate the operation such as setting of the device.

It is possible to configure the cell culture device 10E according to the third embodiment to have a plurality of cell culture units 9E similarly to the cell culture device 10A (refer to FIG. 3) according to the second embodiment. The number of cell culture units 9E may be any number of two or more.

In the plurality of cell culture units 9E, the first liquid storage chambers 1E and 1E of at least two cell culture units 9E and 9E are able to be connected with each other using a gas flow path (not shown in the drawings) so that gas is able to flow therethrough.

In addition, the second liquid storage chambers 2E and 2E of at least the two cell culture units 9E and 9E among the plurality of cell culture units 9E can be connected with each other using a gas flow path (not shown in the drawings) so that gas is able to flow therethrough.

According to this configuration, by pressurizing some first liquid storage chambers 1E of the plurality of first liquid storage chambers 1E in the step 3, all the first liquid storage chambers 1E connected through the gas flow path are capable of being collectively pressurized. In addition, by pressurizing some second liquid storage chambers 2E of the plurality of second liquid storage chambers 2E in the step 4, all the second liquid storage chambers 2E connected through the gas flow path are capable of being collectively pressurized.

Accordingly, it is possible to perform a plurality of tests in parallel through a simple operation.

Fourth Embodiment

[Cell Culture Device]

A cell culture device 10B according to a fourth embodiment will be described with reference to the drawings.

Figure 5:
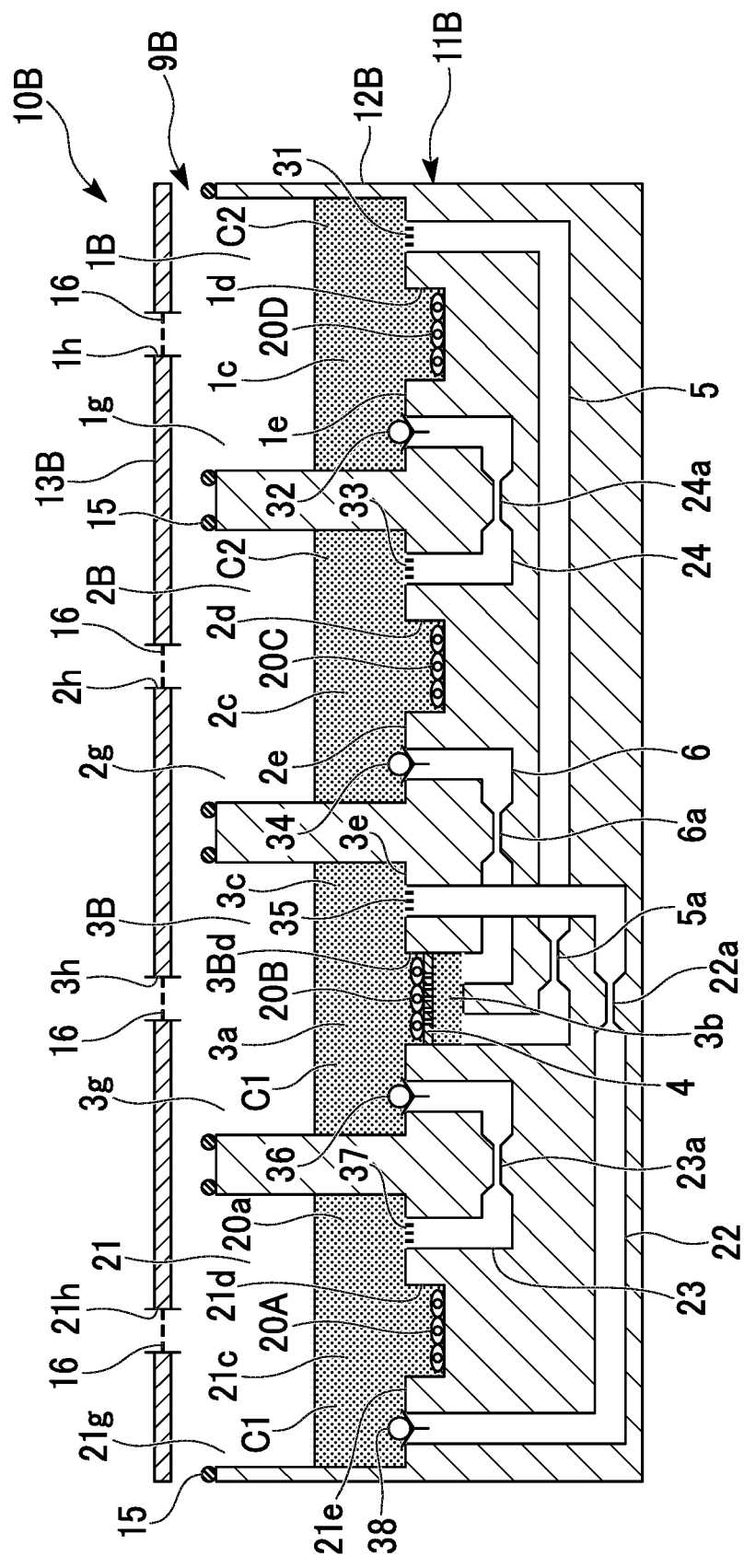
FIG. 5 is a cross-sectional view schematically showing a cell culture device according to a fourth embodiment.
Figure 6:
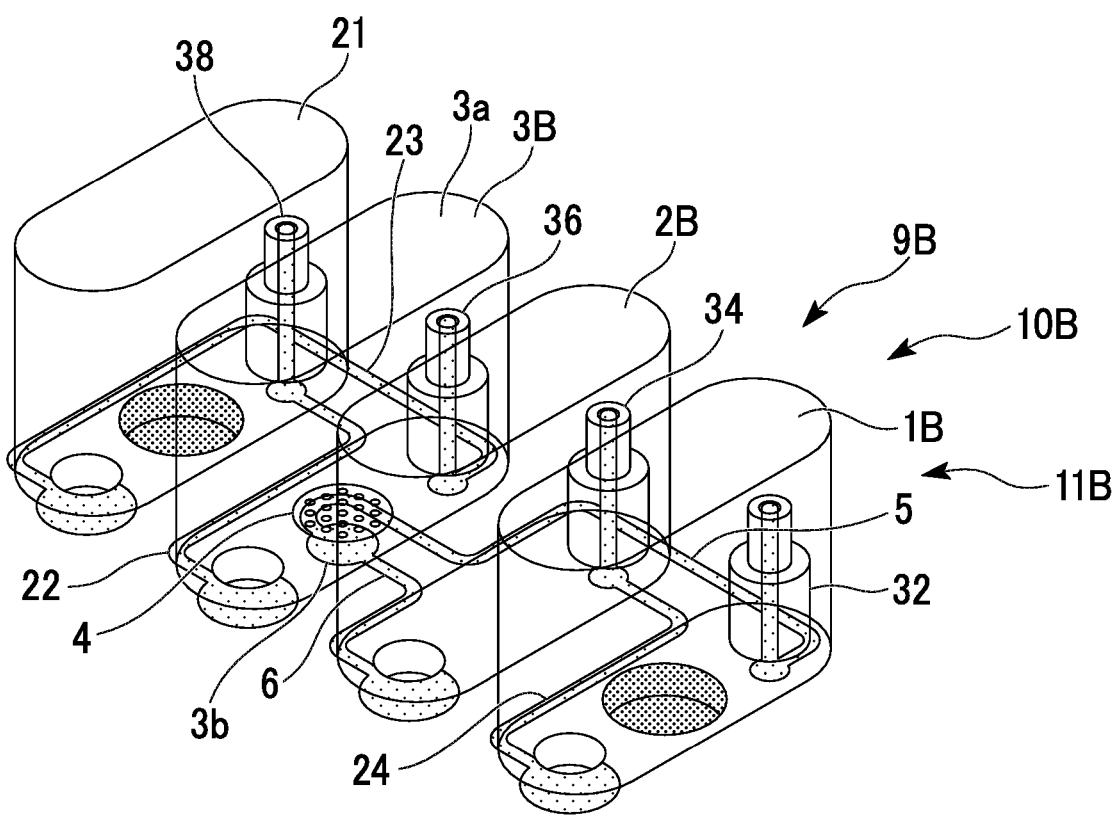
FIG. 6 is a perspective view schematically showing the cell culture device of FIG. 5.
Figure 7:
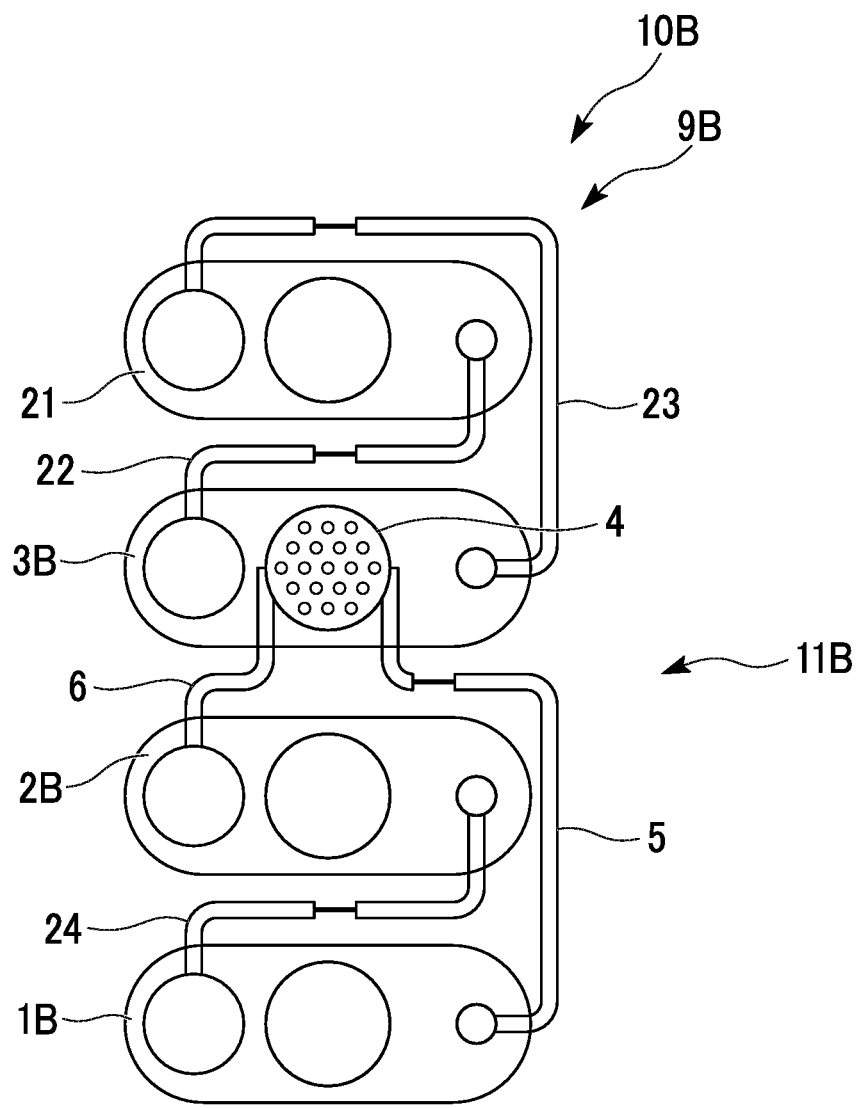
FIG. 7 is a plan view schematically showing the cell culture device of FIG. 5.

FIG. 5 is a cross-sectional view schematically showing the cell culture device 10B. FIG. 6 is a perspective view schematically showing the cell culture device 10B. FIG. 7 is a plan view schematically showing the cell culture device 10B.

As shown in FIGS. 5 to 7, the cell culture device 10B includes a storage tank 11B and a pressurizing pump (not shown in the drawings). The storage tank 11B includes one cell culture unit 9B. The storage tank 11B includes a tank main body 12B and a lid portion 13B.

The cell culture unit 9B has a first liquid storage chamber 1B, a second liquid storage chamber 2B, a first culture liquid storage chamber 3B, a membrane 4, a liquid introduction flow path 5, a liquid lead-out flow path 6, a second culture liquid storage chamber 21, a culture liquid lead-out flow path 22, a culture liquid introduction flow path 23, and a communication flow path 24.

The first liquid storage chamber 1B has a main chamber 1c and a cell-holding recess portion 1d (cell-holding portion) formed on a bottom surface 1e of the main chamber 1c. A culture liquid C2 (liquid) can be stored in the first liquid storage chamber 1B. Cells 20D are held in the cell-holding recess portion 1d.

The second liquid storage chamber 2B has a main chamber 2c and a cell-holding recess portion 2d (cell-holding portion) formed on a bottom surface 2e of the main chamber 2c. The culture liquid C2 can be stored in the first liquid storage chamber 1B. Cells 20C are held in the cell-holding recess portion 2d.

The membrane 4 is provided inside a recess portion 3d (at a position slightly deeper than that of an upper opening of a recess portion 3d) in the first culture liquid storage chamber 3B. The upper portion of the recess portion 3d and the membrane 4 form a cell-holding recess portion 3Bd (cell-holding portion) in which cells 20B are held. The first culture liquid storage chamber 3B is capable of storing a culture liquid C1 in a culture liquid storage space 3a.

The second culture liquid storage chamber 21 has a main chamber 21c and a cell-holding recess portion 21d (cell-holding portion) formed on a bottom surface 21e of the main chamber 21c. The internal space of the second culture liquid storage chamber 21 is a culture liquid storage space 21a. The second culture liquid storage chamber 21 is capable of storing the culture liquid C1 in the culture liquid storage space 21a. Cells 20A are held in the cell-holding recess portion 21d.

One end of the communication flow path 24 is connected to the bottom portion of the main chamber 2c of the second liquid storage chamber 2B, and the other end is connected to the bottom portion of the main chamber 1c of the first liquid storage chamber 1B. The communication flow path 24 is capable of introducing the culture liquid C2 from the second liquid storage chamber 2B into the first liquid storage chamber 1B.

One end of the culture liquid lead-out flow path 22 is connected to the bottom portion of a main chamber 3c of the first culture liquid storage chamber 3B, and the other end is connected to the bottom portion of the main chamber 21c of the second culture liquid storage chamber 21. The culture liquid lead-out flow path 22 is capable of introducing the culture liquid C1 from the first culture liquid storage chamber 3B into the second culture liquid storage chamber 21.

One end of the culture liquid lead-out flow path 22 is connected to the bottom portion of a main chamber 21c of the second culture liquid storage chamber 21, and the other end is connected to the bottom portion of the main chamber 3c of the first culture liquid storage chamber 3B. The culture liquid lead-out flow path 22 is capable of introducing the culture liquid C1 from the second culture liquid storage chamber 21 into the first culture liquid storage chamber 3B.

The lid portion 13B is capable of airtightly closing the opening of the tank main body 12B in an openable manner. Specifically, the lid portion 13B is capable of airtightly closing upper openings 1g, 2g, 3g, and 21g of the first liquid storage chamber 1B, the second liquid storage chamber 2B, the first culture liquid storage chamber 3B, and the second culture liquid storage chamber 21. An example of a structure in which the lid portion 13B airtightly closes the upper openings 1g, 2g, 3g, and 21g includes a structure in which the lid portion 13B abuts on the upper surface of the tank main body 12B with a packing 15 interposed therebetween, and the packing 15 is provided so as to surround each of the upper openings 1g, 2g, 3g, and 21g. In FIG. 5, the lid portion 13B is shown separately from the tank main body 12B.

The lid portion 13B has vent holes 1h, 2h, 3h, and 21h at positions corresponding to the first liquid storage chamber 1B, the second liquid storage chamber 2B, the first culture liquid storage chamber 3B, and the second culture liquid storage chamber 21, respectively. It is preferable that an air filter 16 be provided in each of the vent holes 1h, 2h, 3h, and 21h.

A Laplace valve 31 which allows flow of a liquid from the first liquid storage chamber 1B to the liquid introduction flow path 5 and prevents inflow of gas (for example, air) from the first liquid storage chamber 1B to the liquid introduction flow path 5 is provided at one end of the liquid introduction flow path 5 in the first liquid storage chamber 1B.

A check valve 32 which allows flow of a liquid in a direction from the communication flow path 24 to the first liquid storage chamber 1B and prevents flow in an opposite direction thereof is provided at the other end of the communication flow path 24 in the first liquid storage chamber 1B.

A Laplace valve 33 which allows flow of a liquid from the second liquid storage chamber 2B to the communication flow path 24 and prevents inflow of gas from the second liquid storage chamber 2B to the communication flow path 24 is provided at one end of the communication flow path 24 in the second liquid storage chamber 2B.

A check valve 34 which allows flow of a liquid in a direction from the liquid lead-out flow path 6 to the second liquid storage chamber 2B and prevents flow in an opposite direction thereof is provided at the other end of the liquid lead-out flow path 6 in the second liquid storage chamber 2B.

A Laplace valve 35 which allows flow of a liquid from the first culture liquid storage chamber 3B to the culture liquid lead-out flow path 22 and prevents inflow of gas from the first culture liquid storage chamber 3B to the culture liquid lead-out flow path 22 is provided at one end of the culture liquid lead-out flow path 22 in the first culture liquid storage chamber 3B.

A check valve 36 which allows flow of a liquid in a direction from the culture liquid introduction flow path 23 to the first culture liquid storage chamber 3B and prevents flow in an opposite direction thereof is provided at the other end of the culture liquid introduction flow path 23 in the first culture liquid storage chamber 3B.

A Laplace valve 37 which allows flow of a liquid from the second culture liquid storage chamber 21 to the culture liquid introduction flow path 23 and prevents inflow of gas from the second culture liquid storage chamber 21 to the culture liquid introduction flow path 23 is provided at one end of the culture liquid introduction flow path 23 in the second culture liquid storage chamber 21.

A check valve 38 which allows flow of a liquid in a direction from the culture liquid lead-out flow path 22 to the second culture liquid storage chamber 21 and prevents flow in an opposite direction thereof is provided at the other end of the culture liquid lead-out flow path 22 in the second culture liquid storage chamber 21.

(Check Valve)

An example of the check valves 32, 34, 36, and 38 includes a check valve having a structure including, for example, a valve seat with a valve hole and a valve body. In this check valve, when a liquid flows in a forward direction, the valve hole is opened by separating the valve body from the valve seat. Therefore, the liquid flows in the forward direction while passing through the valve hole. When the liquid flows in an opposite direction, the valve body abuts on the valve seat and the valve hole is closed. Therefore, the flow of the liquid in the opposite direction is prevented.

The check valves 32, 34, 36, and 38 are examples of a backflow prevention mechanism for controlling flow of a liquid.

(Laplace Valve)

Figure 13A:
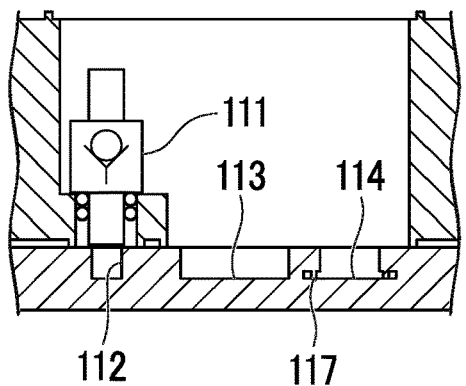
FIG. 13A is an explanatory view of a Laplace valve. Specifically, it is a partially enlarged view of a liquid storage chamber provided with a Laplace valve.
Figure 13B:
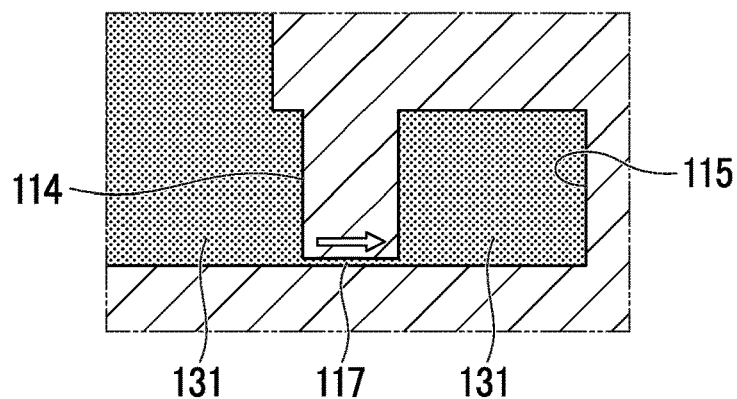
FIG. 13B is an explanatory view of the Laplace valve. Specifically, it is a schematic diagram in a case where a medium flows into a communication flow path from a downstream port through the Laplace valve.
Figure 13C:
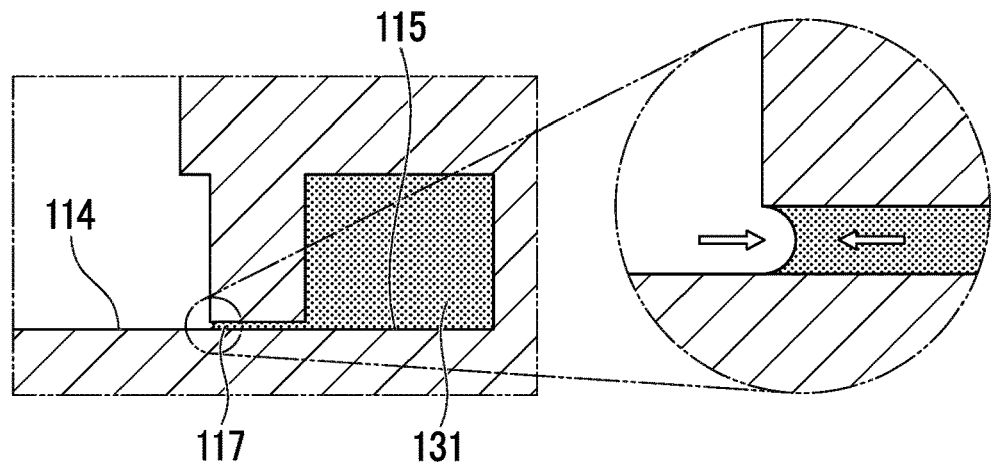
FIG. 13C is an explanatory view of the Laplace valve. Specifically, it shows a schematic diagram in a case where the Laplace valve is functioning when air has flowed into the downstream port.

The structure and function of the Laplace valves 31, 33, 35, and 37 will be described using FIGS. 13A to 13C. FIG. 13A shows a partially enlarged view of a liquid storage chamber provided with a Laplace valve 117. FIG. 13B shows a schematic diagram in a case where a medium 131 flows into a communication flow path 115 from a downstream port 114 through the Laplace valve 117. FIG. 13C shows a schematic diagram in a case where the Laplace valve 117 is functioning when air has flowed into the downstream port 114. As shown in FIG. 13C, a pressure difference due to interfacial tension, that is, Laplace pressure is generated between the medium 131 and air in the micro-flow path. In a case where the surface of the flow path is wet with a liquid medium, air cannot flow into the micro-flow path filled with a liquid under the air pressure condition of less than the Laplace pressure. Under such a condition, the micro-flow path can be treated as a passive air inflow prevention mechanism.

The design of the Laplace valve will be described below.

The pressure (Laplace pressure, critical pressure) ($\Delta P_{Lap}$) at which air flows into the Laplace valve can be calculated by the interfacial tension ($\gamma$), and the width ($w_L$) and the depth ($h_L$) of the micro-flow path constituting the Laplace valve, using Equation (1).

$$\Delta P_{Lap} = 2\gamma(1/w_L + 1/h_L) \quad (1)$$

It is considered that the practical pressure range for driving the cell culture device is determined by the pressure range adjustable with a commercially available pressure control device and the pressure resistance of cells.

If the pressure resistance of cells is an upper limit (30 kPa=225 mmHg) of the blood pressure in a living body, a practical pressure range for driving the cell culture device according to the embodiment is approximately 1 kPa to 30 kPa. In a case where the interfacial tension of a culture liquid is approximately 60 mN/m and the cross section of the micro-flow path constituting the Laplace valve is square, that is, in a case where $w_L = h_L$, the size of the micro-flow path into which air flows at 30 kPa is estimated as approximately $w_L = h_L = 8$ μm and the size of the micro-flow path into which air flows at 1 kPa is estimated as approximately $w_L = h_L = 240$ μm, using Equation (1).

By setting the sizes of the micro-flow path constituting the Laplace valve to be smaller than the above-described sizes ($w_L = h_L = 8$ μm at 30 kPa and $w_L = h_L = 240$ μm at 1 kPa), it is possible to prevent air from flowing into the Laplace valve when the device is operated at an assumed pressure.

That is, if a micro-flow path constituting the Laplace valve is formed so that the Laplace pressure $\Delta P_{Lap}$, which is a critical pressure for the Laplace valve to function, is larger than the pressure range used in the cell culture device according to the embodiment, it is possible to prevent air from flowing into the Laplace valve.

Even in a case where the ratio of $w_L$ to $h_L$ is not 1:1, it is possible to design the size of the flow path based on Equation (1).

In the cell culture device 10B, by respectively designing the widths and the depths of the flow paths 5, 6, 22, 23, and 24, for example, to be 200 μm and 25 μm and estimating the Laplace pressure as 5.4 kPa, it is possible to make a liquid flow through the flow paths 5, 6, 22, 23, and 24 so that the pressure becomes lower than or equal to the value.

The Laplace valves 31, 33, 35, and 37 are examples of a backflow prevention mechanism for controlling flow of a liquid.

(Resistance Flow Path)

The flow rate (Q) and the pressure loss ($\Delta P$) of a liquid flowing through the micro-flow path having a rectangular cross section have the following relationship (refer to F. M. White, Viscous Fluid Flow, McGraw-Hill Companies, Inc, Boston, 2006).

$$\Delta P = R \times Q \quad (2)$$

$$R = \frac{12\mu l}{wh^3} \left\{ 1 - \frac{h}{w}\left[\frac{192}{\pi^5} \sum_{i=1,3,5}^{\infty} \frac{1}{i^5} \tanh\left(\frac{i\pi w}{2h}\right)\right] \right\}^{-1} \quad (3)$$

In Equations (2) and (3), $\Delta P$ represents a pressure difference between an inlet and an outlet of the micro-flow path, R represents a flow path resistance, μ represents a viscosity of a fluid, l represents a length of the micro-flow path, w represents a width of the micro-flow path, and h represents a depth of the micro-flow path. Equations (2) and (3) are established with a condition of w>h.

For example, in the cell culture device 10B, the liquid introduction flow path 5, the liquid lead-out flow path 6, the culture liquid lead-out flow path 22, the culture liquid introduction flow path 23, and the communication flow path 24 may have resistance flow path parts 5a, 6a, 22a, 23a, and 24a of which the flow path cross-sectional areas are less than or equal to ⅒ in order to control the flow rate.

A case where the lengths of the resistance flow path parts are equal to those of parts of other sections in the flow paths 5, 6, 22, 23, and 24 can be considered. In a case where the cross-sectional area of a resistance flow path is ⅒ of the cross-sectional area of the other part, the width w and the depth h become $\frac{1}{10^{0.5}}$ and the flow path resistance R of the resistance flow path of Equation (3) becomes 100 times the flow path resistance R of the part other than the resistance flow path.

Regarding the pressure loss, the pressure loss in the resistance flow path becomes 100 times the pressure loss of the part other than the resistance flow path from Equation (2). When estimating the flow rate through the entire flow path, an estimation error in a case where the flow rate is estimated in consideration of only the resistance of the resistance flow path and the pressure applied to the entire flow path becomes ¹⁄₁₀₀, which can be called an acceptable error.

That is, in a case where a resistance flow path part having a flow path cross-sectional area of less than or equal to ⅒ is provided in a part of the flow path in order to control the flow rate, there is an advantage in that the design of a flow path network becomes easy by designing the flow path in consideration of only the pressure loss in the resistance flow path.

Next, an example of a method of culturing cells using the cell culture device 10B will be described.

(1) Step 1

Figure 8A:
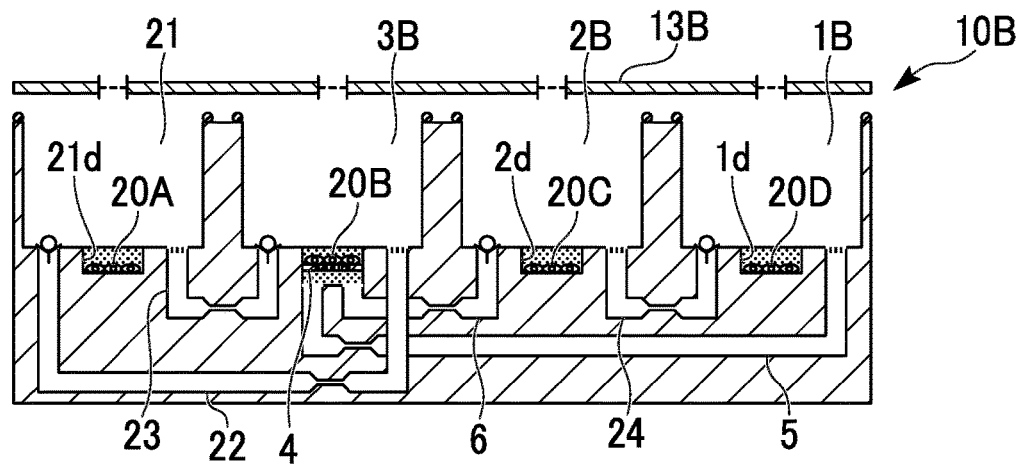
FIG. 8A is a view explaining an example of a cell culture method using the cell culture device of FIG. 5.

As shown in FIG. 8A, the cells 20B are seeded on an inner surface 4a of the membrane 4 in the first culture liquid storage chamber 3B and are made to adhere thereto. The cells 20A, 20C, and 20D are respectively seeded in the cell-holding recess portion 21d of the second culture liquid storage chamber 21, the cell-holding recess portion 2d of the second liquid storage chamber 2B, and the cell-holding recess portion 1d of the first liquid storage chamber 1B.

(2) Step 2

Figure 8B:
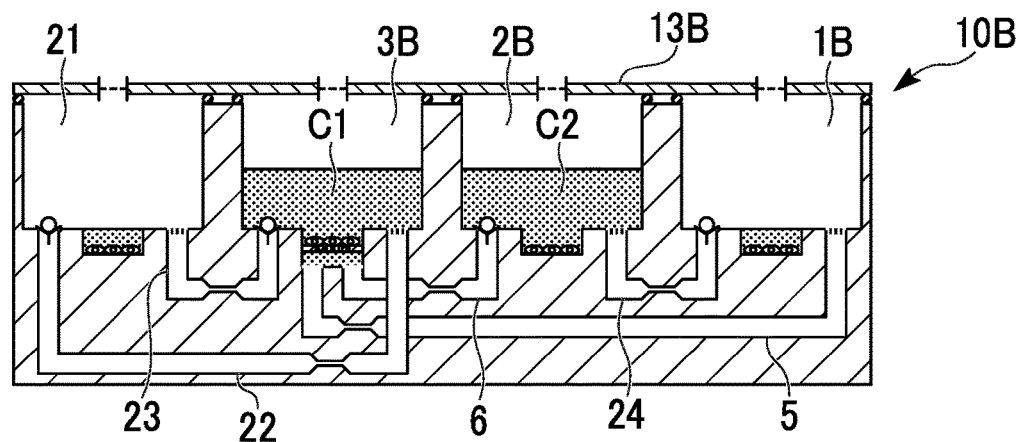
FIG. 8B is a view explaining an example of a cell culture method using the cell culture device of FIG. 5.

As shown in FIG. 8B, culture liquids C1 and C2 are respectively introduced into the first culture liquid storage chamber 3B and the second liquid storage chamber 2B, and the lid portion 13 is closed.

(3) Step 3

Figure 8C:
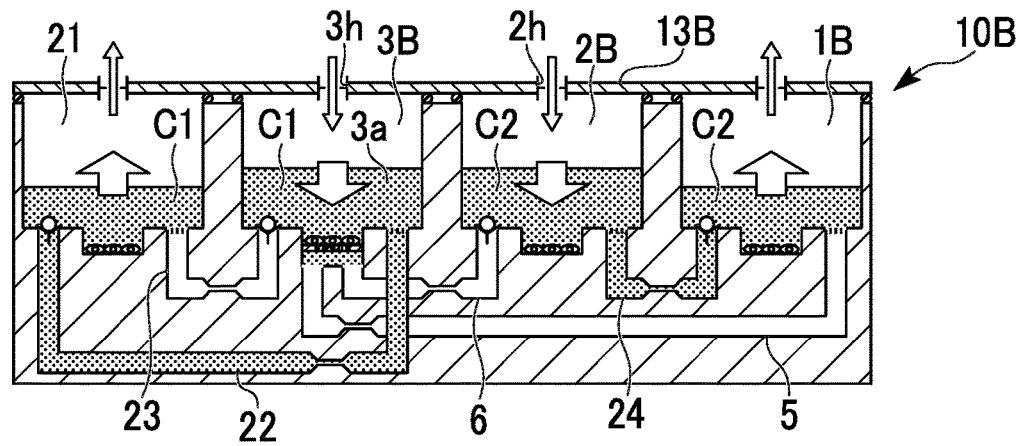
FIG. 8C is a view explaining an example of a cell culture method using the cell culture device of FIG. 5.

As shown in FIG. 8C, gas (for example, air) is supplied to the first culture liquid storage chamber 3B and the second liquid storage chamber 2B through the vent holes 3h and 2h respectively to pressurize the inside of each of the chambers. At this time, it is preferable that the second culture liquid storage chamber 21 and the first liquid storage chamber 1B be open to the atmosphere.

Due to the pressure increase in the first culture liquid storage chamber 3B, the culture liquid C1 in the culture liquid storage space 3a of the first culture liquid storage chamber 3B is introduced into the second culture liquid storage chamber 21 through the culture liquid lead-out flow path 22.

Due to the pressure increase in the second liquid storage chamber 2B, the culture liquid C2 in the second liquid storage chamber 2B is introduced into the first liquid storage chamber 1B through the communication flow path 24.

(4) Step 4

Figure 8D:
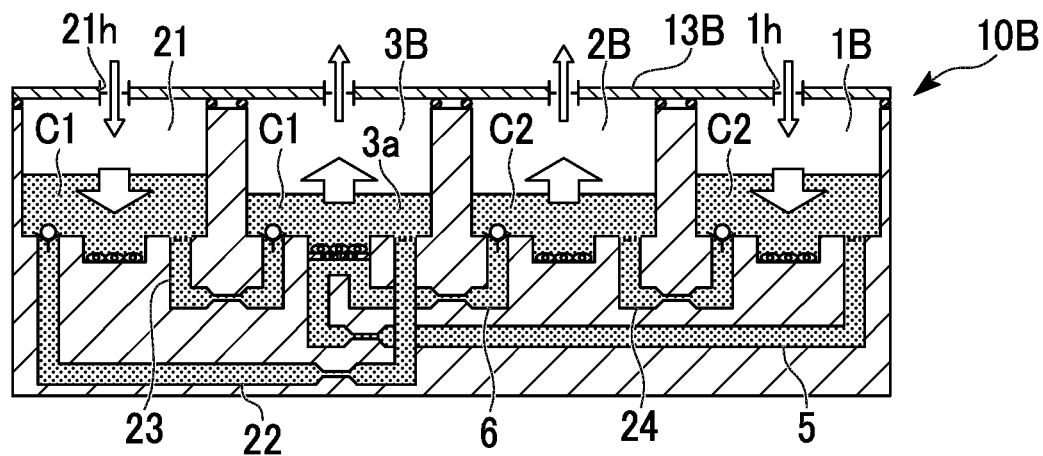
FIG. 8D is a view explaining an example of a cell culture method using the cell culture device of FIG. 5.

As shown in FIG. 8D, gas (for example, air) is supplied to the second culture liquid storage chamber 21 and the first liquid storage chamber 1B through the vent holes 21h and 1h respectively to pressurize the inside of each of the chambers. At this time, it is preferable that the first culture liquid storage chamber 3B and the second liquid storage chamber 2B be open to the atmosphere.

Due to the pressure increase in the second culture liquid storage chamber 21, the culture liquid C1 in the second culture liquid storage chamber 21 is introduced into the culture liquid storage space 3a of the first culture liquid storage chamber 3B through the culture liquid introduction flow path 23.

Due to the pressure increase in the first liquid storage chamber 1B, the culture liquid C2 in the first liquid storage chamber 1B is introduced into the second liquid storage chamber 2B through the liquid introduction flow path 5, an outer surface side space 3b, and the liquid lead-out flow path 6.

By repeating the steps 3 and 4, it is possible to circulate the culture liquids C1 and C2 in the cell culture device 10B.

In the cell culture device 10B, it is possible to collectively perform evaluation of four types of cells 20A to 20D.

For example, if the cells 20A to 20D are respectively gastrointestinal cells, intestinal cells, cancer cells, and normal cells, it is possible to evaluate digestion and absorption, anticancer effect, and side effects of an anticancer agent at the same time.

In the cell culture device 10B, it is possible to circulate the culture liquids C1 and C2 between the first culture liquid storage chamber 3B and the second culture liquid storage chamber 21. Therefore, it is possible to culture the cells 20A to 20D in an environment where a shearing force is applied.

Fifth Embodiment

[Cell Culture Device]

A cell culture device 10C according to a fifth embodiment will be described with reference to the drawings.

Figure 9:
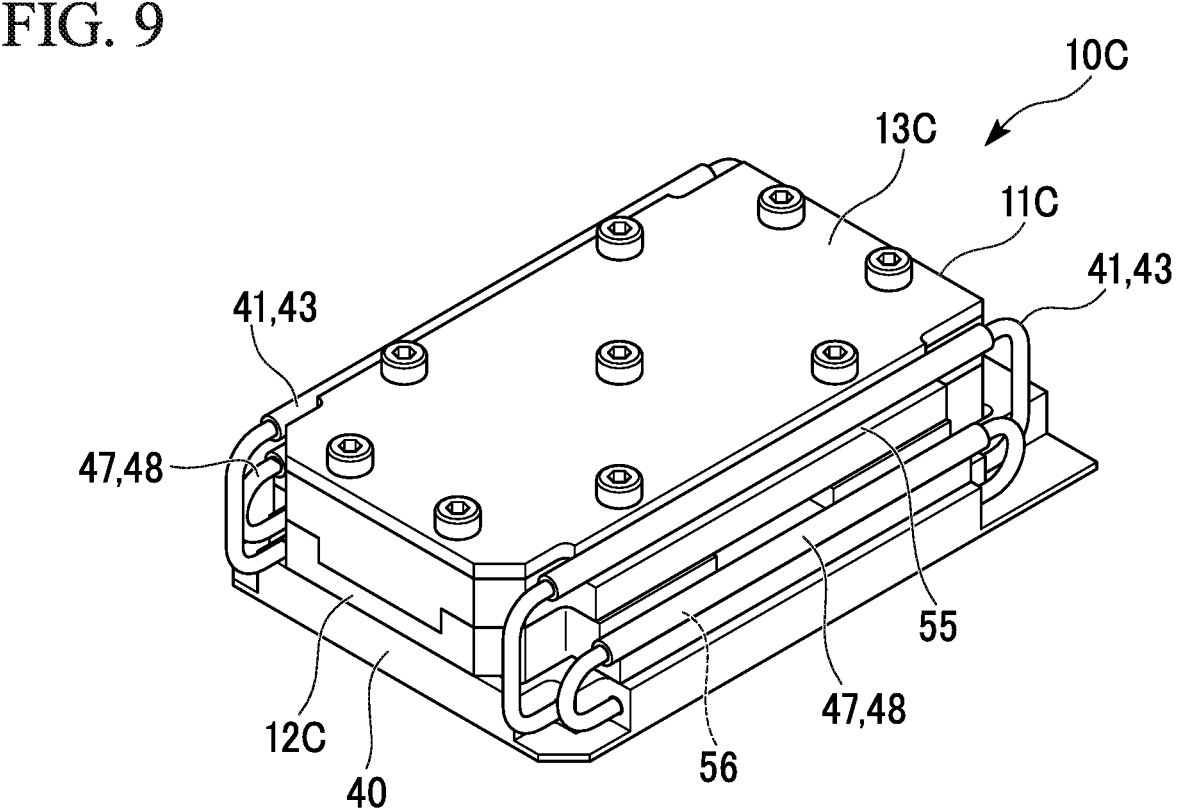
FIG. 9 is a perspective view showing a cell culture device according to a fifth embodiment.
Figure 10:
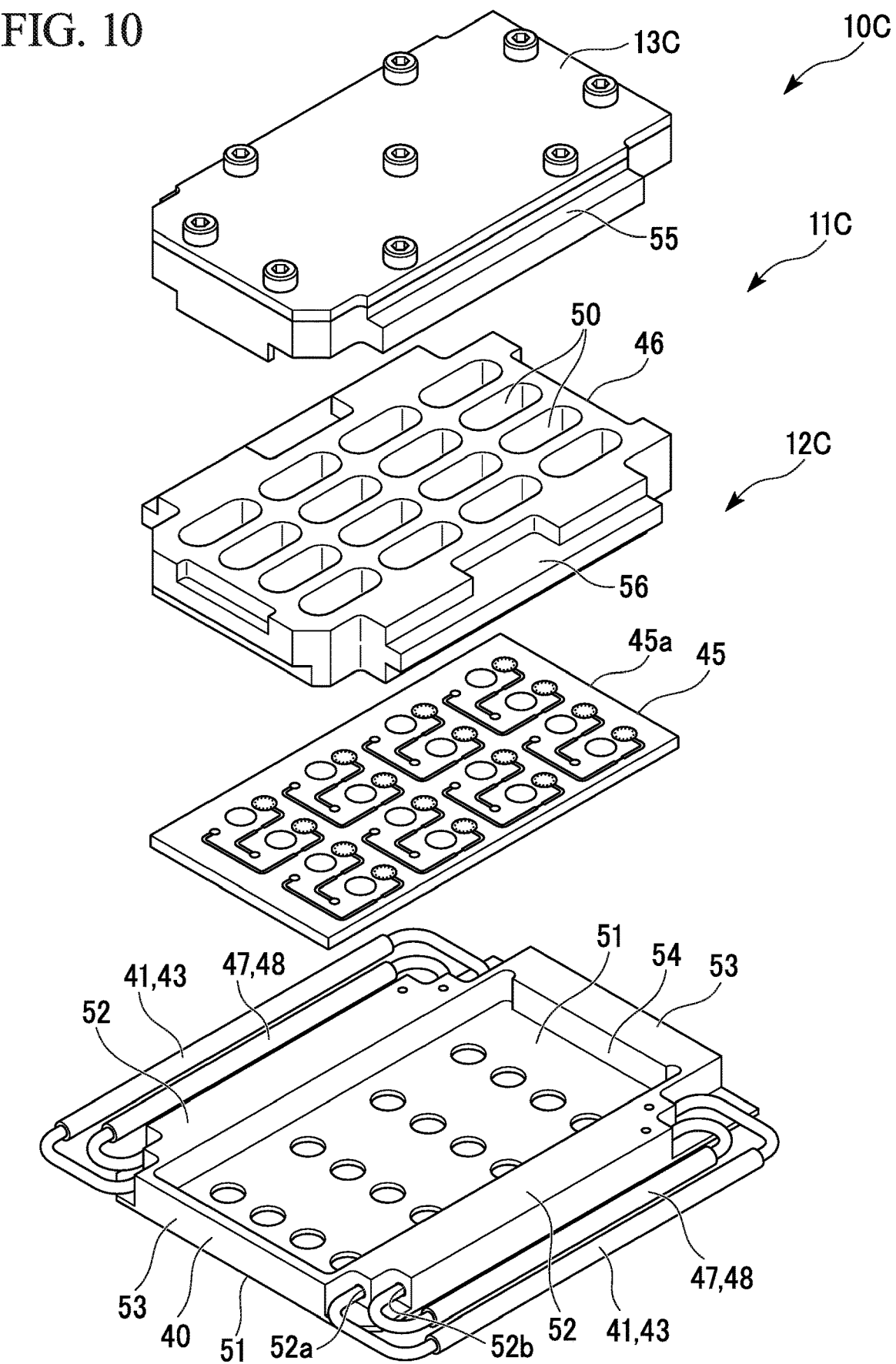
FIG. 10 is an exploded perspective view showing the cell culture device of FIG. 9.
Figure 11A:
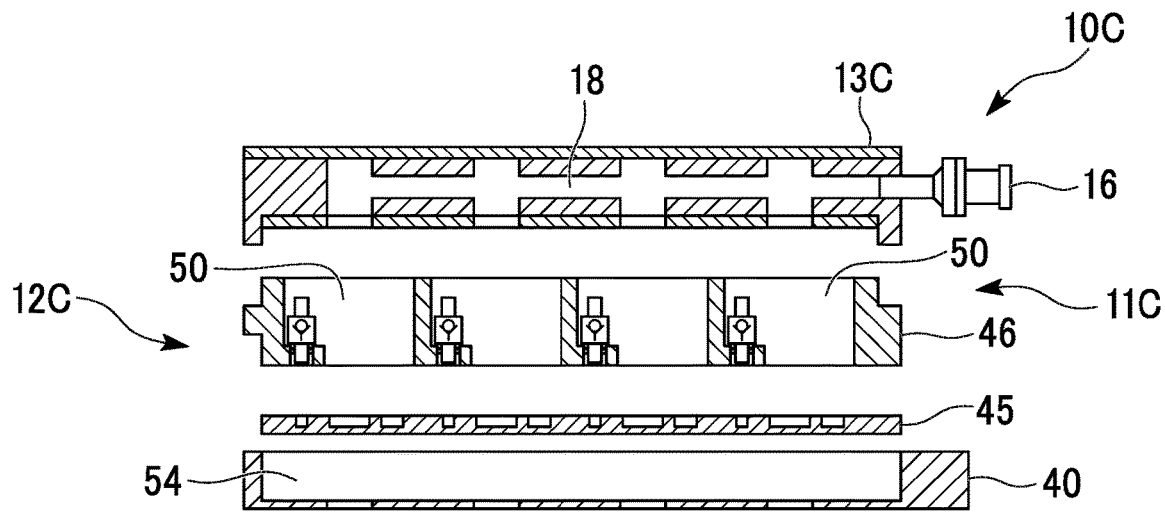
FIG. 11A is a front cross-sectional view of the cell culture device of FIG. 9 in a disassembled state.
Figure 11B:
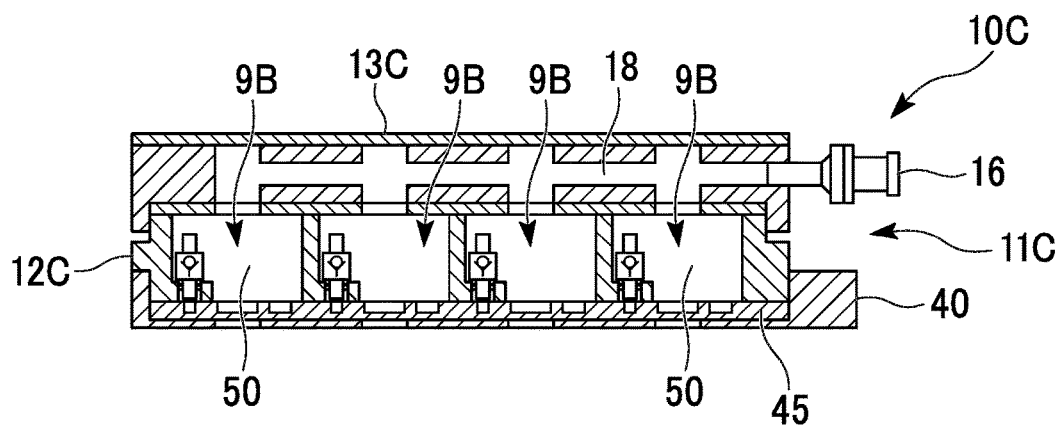
FIG. 11B is a front cross-sectional view of the cell culture device of FIG. 9.
Figure 12A:
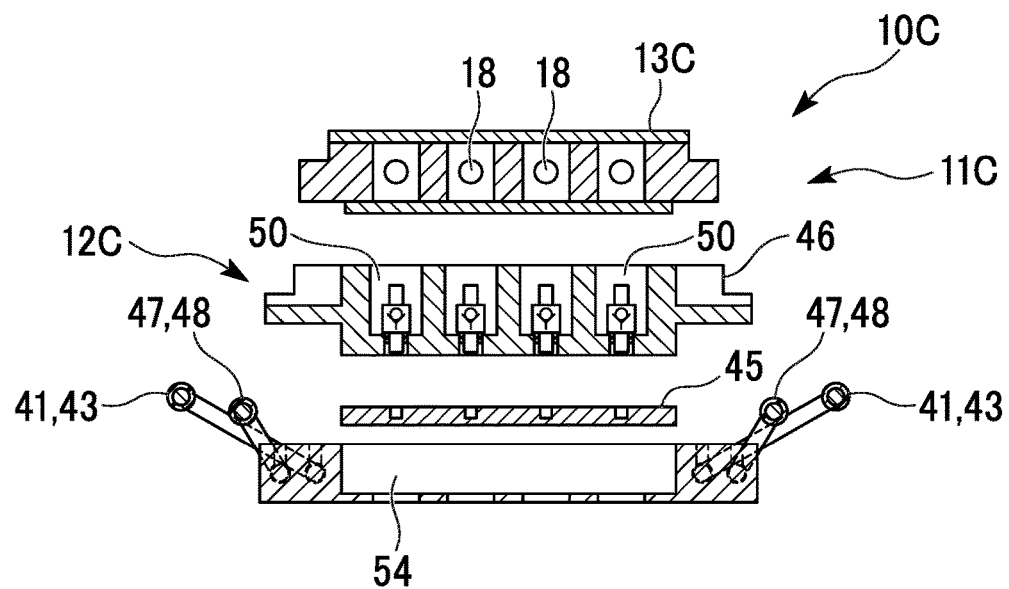
FIG. 12A is a side cross-sectional view of the cell culture device of FIG. 9 in a disassembled state.
Figure 12B:
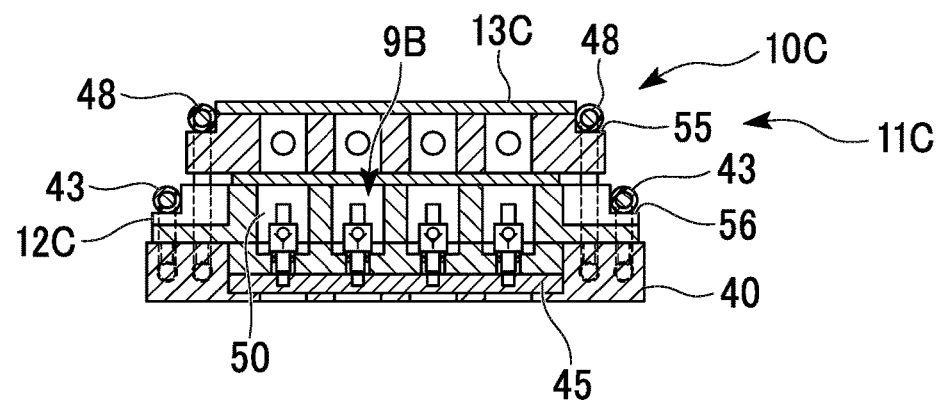
FIG. 12B is a side cross-sectional view of the cell culture device of FIG. 9.

FIG. 9 is a perspective view showing the cell culture device 10C. FIG. 10 is an exploded perspective view showing the cell culture device 10C. FIG. 11A is a front cross-sectional view of the cell culture device 10C in a disassembled state. FIG. 11B is a front cross-sectional view of the cell culture device 10C. FIG. 12A is a side cross-sectional view of the cell culture device 10C in a disassembled state. FIG. 12B is a side cross-sectional view of the cell culture device 10C.

As shown in FIGS. 9 to 12B, the storage tank 11C of the cell culture device 10C includes a plurality of cell culture units 9B (refer to FIGS. 5 and 6).

The storage tank 11C includes a tank main body 12C, a lid portion 13C, a base body portion 40, a lid portion-pressing portion 41, and a wall portion-pressing portion 47.

The base body portion 40 includes a base plate 51, thick portions 52 and 52 formed so as to protrude upward from side edges of the base plate 51, and end wall portions 53 and 53 formed so as to protrude upward from end edges of the base plate 51.

The base plate 51, the thick portions 52 and 52, and the end wall portions 53 and 53 define an accommodation space 54 for accommodating a bottom plate 45. An insertion hole 52a into which an end portion of a pressing bar 43 is inserted and an insertion hole 52b into which an end portion of a pressing bar 48 is inserted are formed on both end surfaces of the thick portion 52. The base body portion 40 supports the tank main body 12C placed on the base plate 51.

The lid portion-pressing portion 41 has a pair of pressing bars 43 (pressing members) for pressing the lid portion 13 toward the tank main body 12C. The pressing bar 43 is capable of moving rotationally around a central axis along the thick portion 52 in an axial direction in a state in which the both end portions are inserted into the insertion holes 52a, using the insertion portions as supporting points. The pressing bars 43 are capable of being engaged with engaging recess portions 55 formed on both side portions of the upper surface of the lid portion 13C. Accordingly, it is possible to hold the lid portion 13C in a state where the lid portion is pressed against the tank main body 12C and seal the internal space of the tank main body 12C.

The tank main body 12C includes a bottom plate 45 and a block-shaped wall portion 46 provided on an upper surface 45a (one surface) of the bottom plate 45.

The wall portion 46 has a plurality of through-hole portions 50 penetratingly formed in a thickness direction. The first liquid storage chamber 1B, the second liquid storage chamber 2B, the first culture liquid storage chamber 3B, and the second culture liquid storage chamber 21 are spaces partitioned by the through-hole portions 50 and the bottom plate 45. Each of the shapes in the plan views of the chambers 1B, 2B, 3B, and 21 is oval.

A liquid introduction flow path 5, a liquid lead-out flow path 6, a culture liquid lead-out flow path 22, and a culture liquid introduction flow path 23 are formed in the bottom plate 45 (refer to FIG. 7).

The wall portion-pressing portion 47 has the pressing bar 48 (pressing member) for pressing the wall portion 46 toward the bottom plate 45. The pressing bar 48 is formed of, for example, metal, and is capable of moving rotationally around a central axis along the thick portion 52 in an axial direction in a state in which the both end portions are inserted into the insertion holes 52b, using the insertion portions as supporting points. The pressing bars 48 are capable of being engaged with engaging recess portions 56 formed on both side portions of the wall portion 46. Accordingly, it is possible to closely attach the wall portion 46 to the bottom plate 45 without any gap by pressing the wall portion to the bottom plate 45. The wall portion-pressing portion 47 is capable of holding the wall portion 46 in a state in which the wall portion is pressed against the bottom plate 45 using the pressing bar 48.

As shown in FIGS. 11A and 11B, it is preferable that at least two of the first liquid storage chambers 1 in the plurality of cell culture units 9B in the cell culture device 10C be connected with each other using a gas flow path 18. In addition, it is preferable that at least two of the second liquid storage chambers 2 in the plurality of cell culture units 9B be connected with each other using a gas flow path (not shown in the drawings). In addition, it is preferable that at least two of the first culture liquid storage chambers 3B in the plurality of cell culture units 9B be connected with each other using a gas flow path (not shown in the drawings). In addition, it is preferable that at least two of the second culture liquid storage chambers 21 in the plurality of cell culture units 9B be connected with each other using a gas flow path (not shown in the drawings).

In the cell culture device 10C, since the plurality of cell culture units 9B are connected with each other using the gas flow path 18 formed in the lid portion 13C, it is possible to collectively pressurize the storage chambers in the plurality of cell culture units 9B. For example, it is possible to collectively pressurize a plurality of first liquid storage chambers 1. Similarly, it is also possible to collectively pressurize the second liquid storage chamber 2, the first culture liquid storage chamber 3B, and the second culture liquid storage chamber 21. For this reason, in the cell culture device 10C, it is possible to perform tests in the plurality of cell culture units 9B in parallel through a simple operation.

It is possible to use, for example, resin (plastic) or glass for the tank main body 12C and the lid portion 13C. Since it is easy to observe cells optically, it is preferable that the material be a transparent material and specifically preferably resin and glass.

Examples of resin include silicone resin (for example, polydimethylsiloxane (PDMS)), acrylic resin (for example, polymethyl methacrylate (PMMA)), styrene resin (for example, polystyrene), polyvinyl pyridine resin (such as poly(4-vinyl pyridine) or a 4-vinyl pyridine-styrene copolymer), polyolefin resin (for example, polyethylene resin, polypropylene resin, and polymethyl pentene resin), polyester resin (polyethylene terephthalate resin (PET)), polycarbonate resin, and epoxy resin.

Among these, silicone resin (for example, polydimethylsiloxane (PDMS)), acrylic resin (for example, polymethyl methacrylate (PMMA)), and styrene resin (for example, polystyrene) are preferable since they have high transparency.

Since the cell culture device 10C has the plurality of cell culture units 9B, it is possible to perform a plurality of tests in parallel. In addition, since the structure of the device can be simplified, it is possible to miniaturize the device by simplifying the structure of the device and to facilitate the operation such as setting of the device.

The cell culture device 10C is excellent in that it is possible to efficiently evaluate a large number of specimens (drugs and the like) through a simple operation.

Sixth Embodiment

[Cell Culture Device]

A cell culture device 10D according to a sixth embodiment will be described with reference to the drawings.

Figure 14:
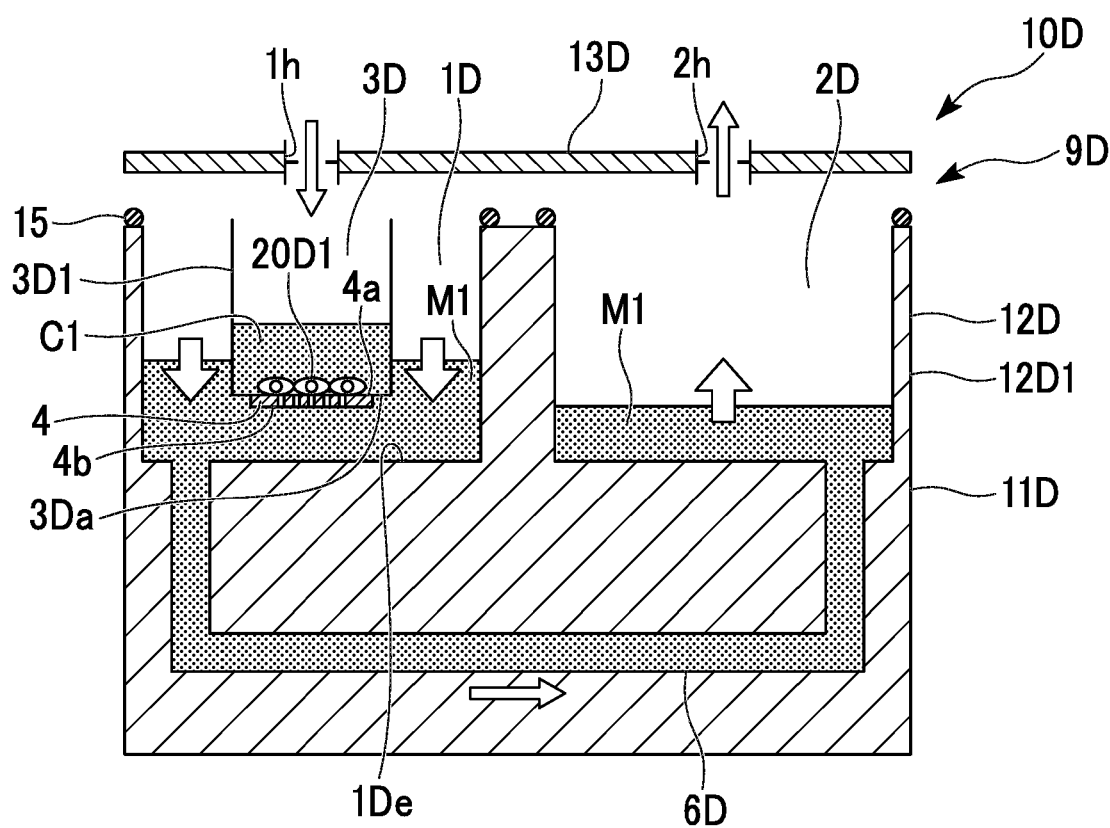
FIG. 14 is a cross-sectional view schematically showing a cell culture device according to a sixth embodiment.

As shown in FIG. 14, a storage tank 11D of the cell culture device 10D includes a tank main body 12D and a lid portion 13D. The storage tank 11D includes a cell culture unit 9D. The cell culture unit 9D has a first liquid storage chamber 1D, a second liquid storage chamber 2D, a culture liquid storage chamber 3D, a membrane 4, and a liquid lead-out flow path 6D.

The tank main body 12D includes a main portion 12D1 in which the first liquid storage chamber 1D and the second liquid storage chamber 2D are formed, and a culture liquid storage tank 3D1. The culture liquid storage chamber 3D is an internal space of the culture liquid storage tank 3D1.

The membrane 4 is provided in a bottom portion 3Da of the culture liquid storage tank 3D1. Cells 20D1 are seeded on an inner surface 4a of the membrane 4.

The culture liquid storage tank 3D1 is accommodated in the first liquid storage chamber 1D. The culture liquid storage tank 3D1 is positioned upwardly away from a bottom surface 1De of the first liquid storage chamber 1D. For this reason, the space between the bottom surface 1De of the first liquid storage chamber 1D and the membrane 4 is a space on an outer surface 4b side of the membrane 4.

The lid portion 13D has vent holes 1h and 2h at positions corresponding to the first liquid storage chamber 1D and the second liquid storage chamber 2D, respectively.

The inside of the first liquid storage chamber 1D is pressurized by supplying gas (for example, air) to the first liquid storage chamber 1D through the vent hole 1h of the lid portion 13D. The second liquid storage chamber 2D is open to the atmosphere through the vent hole 2h. Due to the pressure increase in the first liquid storage chamber 1D, a liquid medium M1 in the first liquid storage chamber 1D is introduced into the second liquid storage chamber 2D through the liquid lead-out flow path 6D.

In the cell culture device 10D, the structure of the flow paths for liquid transfer can be simplified. Therefore, it is possible to miniaturize the device by simplifying the structure of the device and to facilitate the operation such as setting of the device.

The configurations, the combinations thereof, and the like in the above-described embodiments are merely examples, and addition, omission, replacement, and other modifications of the configurations can be made within the scope not departing from the present invention. In addition, the present invention is not limited by each embodiment, but is limited only by the scope of the claims.

For example, although the storage tank 11C of the cell culture device 10C shown in FIG. 9 and the like has the tank main body 12C and the lid portion 13C which are mutually separate bodies, the present invention is not limited thereto, and an integral storage tank may be employed.

The present embodiment is useful in the cell engineering field, the regenerative medical field, the bio-related industry field, the tissue engineering field, and the like. In particular, the present embodiment is useful for development of pharmaceutical products and basic research of cell biology.

DESCRIPTION OF REFERENCE NUMERAL 1, 1B, 1D, 1E first liquid storage chamber
1d, 2d, 2Ed, 21d, 3Bd cell-holding recess portion (cell-holding portion)
1h, 2h, 21h vent hole
2, 2B, 2D, 2E second liquid storage chamber
3, 3B, 3D, 3E culture liquid storage chamber
3a culture liquid storage space
4 membrane 4a inner surface (one surface)
5 liquid introduction flow path
6, 6E, 6D liquid lead-out flow path
6a resistance flow path part
7 liquid return flow path
9, 9B, 9D, 9E cell culture unit
10, 10A, 10B, 10C, 10D, 10E cell culture device
11, 11A, 11B, 11C, 11D, 11E storage tank
12, 12B, 12C, 12D, 12E tank body
13, 13B, 13C, 13D, 13E lid portion
14 pressurizing pump (pressurizing means)
21 second culture liquid storage chamber
22 culture liquid lead-out flow path
23 culture liquid introduction flow path
34, 36, 38 check valve
35 Laplace valve
41 lid portion-pressing portion
43 pressing bar (pressing member)
45 bottom plate
46 wall portion
47 wall portion-pressing portion
48 pressing bar (pressing member)
C1, C2 culture liquid
M1 liquid medium (liquid)

The invention claimed is:

1. A cell culture device, comprising:
a storage tank having a plurality of cell culture units and a gas flow path,
wherein each of the cell culture units comprises:
  a first liquid storage chamber having an airtight structure, in which a liquid is to be stored,
  a second liquid storage chamber in which the liquid is to be stored,
  a culture liquid storage chamber having a culture liquid storage space in which a culture liquid of cells is to be stored,
  a permeable membrane having one surface to which the cells are able to adhere, said one face facing the culture liquid storage space, and
  a liquid lead-out flow path that introduces the liquid from a space on the other surface side of the membrane into the second liquid storage chamber, the first liquid storage chamber being a supply source of the liquid,
wherein the storage tank has a vent hole through which gas is supplied to and discharged from the first liquid storage chamber, and
wherein the gas flow path is provided between at least two of the first liquid storage chambers in the plurality of the cell culture units connected with each other so that gas is able to flow therethrough, and
the gas flow path is configured to collectively transfer the liquid among the plurality of the cell culture units using the gas flow path.

2. The cell culture device according to claim 1, further comprising:
a liquid return flow path which introduces the liquid from the second liquid storage chamber into the first liquid storage chamber,
wherein the second liquid storage chamber has a cell-holding portion in which seeded cells are to be held.

3. The cell culture device according to claim 2,
wherein at least two of the first liquid storage chambers in the plurality of the cell culture units are connected with each other so that gas is able to flow therethrough and at least two of the second liquid storage chambers in the plurality of the cell culture units are connected with each other so that gas is able to flow therethrough.

4. The cell culture device according to claim 1,
wherein each of the cell culture units further includes
  a second culture liquid storage chamber in which the culture liquid is stored,
  a culture liquid lead-out flow path that introduces the culture liquid from the culture liquid storage chamber into the second culture liquid storage chamber, and
  a culture liquid introduction flow path that introduces the culture liquid from the second culture liquid storage chamber into the culture liquid storage chamber, and
wherein the storage tank has a vent hole through which gas is supplied to and discharged from the culture liquid storage chamber.

5. The cell culture device according to claim 4,
wherein at least two of the second culture liquid storage chambers in the plurality of the cell culture units are connected with each other so that gas is able to flow therethrough.

6. The cell culture device according to claim 4,
wherein the first liquid storage chamber, the second liquid storage chamber, and the second culture liquid storage chamber each have a cell-holding portion in which seeded cells are to be held.

7. The cell culture device according to claim 1, further comprising:
a backflow prevention mechanism that controls flow of the liquid from the liquid lead-out flow path to the second liquid storage chamber.

8. The cell culture device according to claim 7,
wherein the backflow prevention mechanism is a check valve which allows the flow of the liquid in a direction from the liquid lead-out flow path to the second liquid storage chamber and prevents flow in an opposite direction thereof.

9. The cell culture device according to claim 1, further comprising:
a liquid introduction flow path that introduces the liquid from the first liquid storage chamber into a space on the other surface side of the membrane; and
a backflow prevention mechanism that controls flow of the liquid from the first liquid storage chamber to the liquid introduction flow path.

10. The cell culture device according to claim 9,
wherein the backflow prevention mechanism is a Laplace valve which allows the flow of the liquid from the first liquid storage chamber to the liquid introduction flow path and prevents flow of gas from the first liquid storage chamber to the liquid introduction flow path.

11. The cell culture device according to claim 1,
wherein the liquid lead-out flow path has a resistance flow path part of which a flow path cross-sectional area is less than or equal to 1/10 of that of the other part.

12. The cell culture device according to claim 1,
wherein the storage tank has a container-shaped tank main body in which the first liquid storage chamber, the second liquid storage chamber, and the culture liquid storage chamber are formed, and a lid portion that airtightly closes openings of the first liquid storage chamber, the second liquid storage chamber, and the culture liquid storage chamber in an openable manner.

13. The cell culture device according to claim 12, further comprising:
a lid portion-pressing portion that holds the lid portion by pressing the lid portion toward the tank main body,
wherein the lid portion-pressing portion has a pressing member that presses the lid portion toward the tank main body.

14. The cell culture device according to claim 12,
wherein the tank main body includes a bottom plate having the liquid lead-out flow path, and a wall portion provided on one surface of the bottom plate, and
wherein the first liquid storage chamber, the second liquid storage chamber, and the culture liquid storage chamber are spaces partitioned by the bottom plate and the wall portion.

15. The cell culture device according to claim 14, further comprising:
a wall portion-pressing portion that holds the wall portion by pressing the wall portion toward the bottom plate,
wherein the wall portion-pressing portion has a pressing member that presses the wall portion toward the bottom plate.

16. The cell culture device according to claim 1, further comprising:
pressurizing means capable of pressurizing an inside of the first liquid storage chamber.

17. A cell culture method, using the cell culture device according to claim 1, the method comprising:
supplying gas to the first liquid storage chamber through the vent hole to pressurize an inside of the first liquid storage chamber; and
introducing the liquid from a space on the other surface side of the membrane into the second liquid storage chamber through the liquid lead-out flow path with a pressure increase in the first liquid storage chamber.

* * * * *